US012678187B2

(12) United States Patent
McGovern et al.

(10) Patent No.: US 12,678,187 B2
(45) Date of Patent: Jul. 14, 2026

(54) SYSTEM AND METHOD FOR HARVESTING A TENDON

(71) Applicants:Smith & Nephew, Inc., Memphis, TN (US); Smith & Nephew Orthopaedics AG, Zug (CH); Smith & Nephew Asia Pacific Pte Limited, Singapore (SG)

(72) Inventors: Paul McGovern, Hanson, MA (US); Ali Hosseini, Quincy, MA (US); Chun Liu, Brookline, MA (US); Rick Fu, Randolph, MA (US); Christopher D. MacCready, Medfield, MA (US); Geoffrey I. Karasic, Raynham, MA (US); Carrie D. Burgess, Jamaica Plain, MA (US); Belin Mirabile, Brookline, MA (US)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 817 days.

(21) Appl. No.: 18/008,521

(22) PCT Filed: Jun. 9, 2021

(86) PCT No.: PCT/US2021/036566

§ 371 (c)(1),
(2) Date: Dec. 6, 2022

(87) PCT Pub. No.: WO2021/252596

PCT Pub. Date: Dec. 16, 2021

(65) Prior Publication Data

US 2023/0210551 A1     Jul. 6, 2023

Related U.S. Application Data

(60) Provisional application No. 63/156,187, filed on Mar. 3, 2021, provisional application No. 63/036,562, filed on Jun. 9, 2020.

(51) Int. Cl.
| | | |
|---|---|---|
| *A61B 17/3205* | (2006.01) | |
| *A61B 17/02* | (2006.01) | |
| *A61B 17/32* | (2006.01) | |

(52) U.S. Cl.
CPC ...... *A61B 17/3205* (2013.01); *A61B 17/0218* (2013.01); *A61B 2017/320052* (2013.01)

(58) Field of Classification Search
CPC ............. A61B 17/00008; A61B 17/02; A61B 17/0218; A61B 17/3205; A61B 17/32053;
(Continued)

(56) References Cited

U.S. PATENT DOCUMENTS

| | | | | |
|---|---|---|---|---|
| 6,196,968 | B1 * | 3/2001 | Rydin | ................... A61B 17/02 |
| | | | | 600/245 |
| 6,511,494 | B1 | 1/2003 | Knighton et al. | |
| 2017/0252056 | A1 * | 9/2017 | Garvey | ................. A61B 17/32 |

FOREIGN PATENT DOCUMENTS

| | | |
|---|---|---|
| JP | 2002524182 B2 | 8/2002 |
| JP | 2008529632 A | 8/2008 |

(Continued)

*Primary Examiner* — Diane D Yabut
*Assistant Examiner* — Christian D Knauss
(74) *Attorney, Agent, or Firm* — Kate Ryland Tetzlaff

(57) ABSTRACT

A system for harvesting a tendon graft is disclosed, including a retractor, a guide and a harvesting tool. The retractor is collapsible and upon release, becomes self-supporting to hold open an anatomic space developed in a patient above the tendon. A guide assembles with the retractor to orient a guide shaft along the retractor and thereby the anatomic space. The harvesting tool includes a working end with a blade edge for cutting into the tendon. The harvesting tool defines a contoured surface for engaging and translating along the guide shaft while assembled to the retractor. The (Continued)

guide shaft and contoured surface limit the trajectory and translation extent of the harvesting tool along and into the tendon.

18 Claims, 30 Drawing Sheets

(58) Field of Classification Search
    CPC ....... A61B 2017/320044; A61B 2017/320052; A61B 2017/320056; A61B 2017/32113
    See application file for complete search history.

(56)                  References Cited

FOREIGN PATENT DOCUMENTS

| WO | 2000015116 A1 | 3/2000 |
| WO | 2006085090 A2 | 8/2006 |
| WO | 2020072766 A1 | 4/2020 |

\* cited by examiner

FIG. 7C                 FIG. 7D

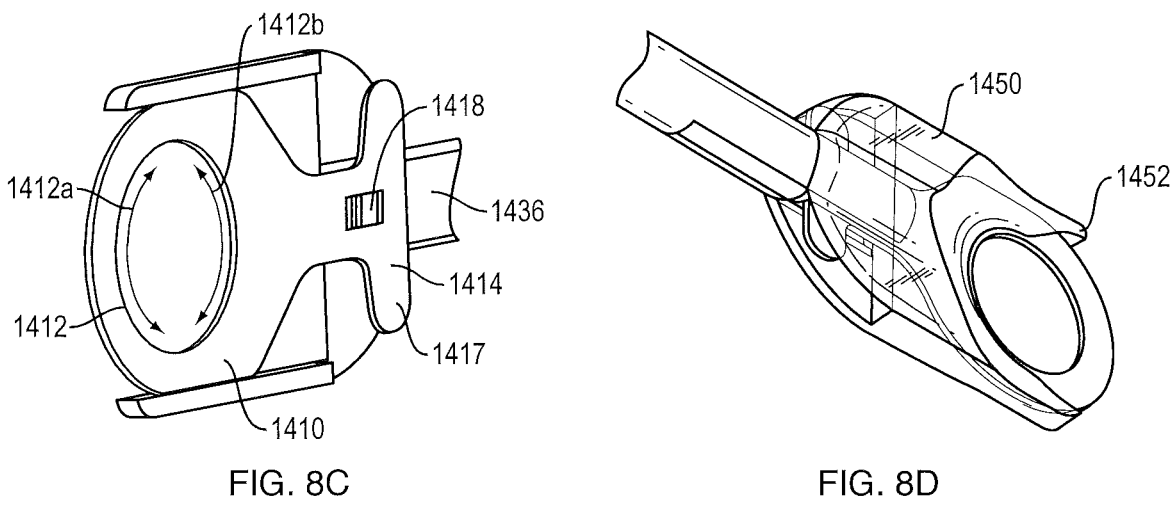
FIG. 8C
FIG. 8D
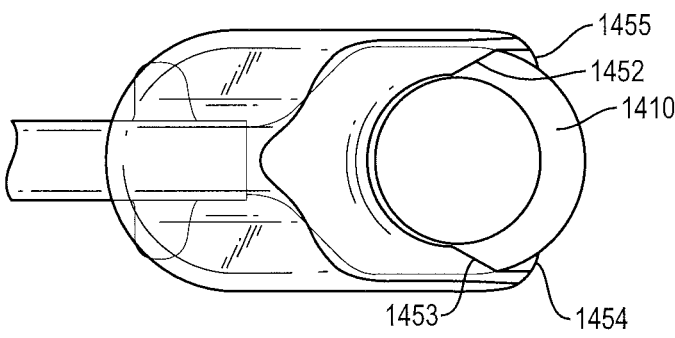
FIG. 8E
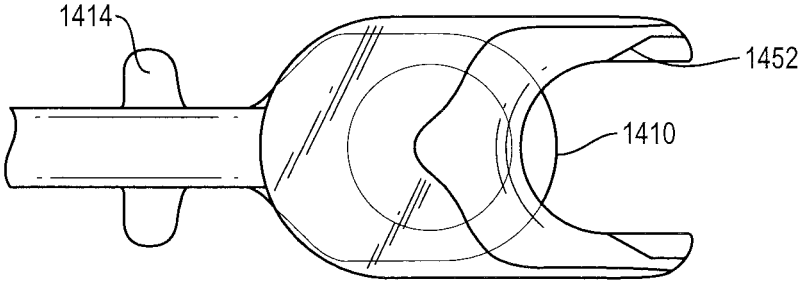
FIG. 8F

SYSTEM AND METHOD FOR HARVESTING A TENDON

CROSS-REFERENCE TO RELATED APPLICATIONS

This application claims benefit to and incorporates by reference in their entirety, U.S. Provisional Patent No. 63/036,562 filed Jun. 9, 2020; titled "SYSTEM FOR TENDON HARVESTING" and U.S. Provisional Patent No. 63/156,187 filed Mar. 3, 2021; titled "SYSTEM AND METHOD FOR HARVESTING A TENDON".

This application is related to International Patent Application filed Oct. 16, 2020 and titled "TENDON HARVESTING ASSEMBLIES AND METHODS"; commonly owned and herein incorporated by reference in its entirety.

FIELD

The present disclosure relates to a system and method for harvesting a tendon, and in particular for harvesting a Quadriceps Tendon (QT).

BACKGROUND

The quadriceps tendon is often used as a source of tissue graft for ligament surgery, such as anterior cruciate ligament (ACL) reconstruction. However, graft harvesting from the QT presents several challenges, as the QT is larger and stronger than other tendons, resulting in a tough fibrous bundle of tissue that tends to resists accurate consistent dissection. Furthermore, in order to reduce incisions around the target area, harvesting is preferably performed though a small incision near the knee. This may result in a second person retracting the skin away from the anterior QT surface while the surgeon wrestles with this tendon tissue. Existing devices may require multiple cuts to dissect this tough tissue. The fibrous tendon tissue may deviate related art devices from their intended cutting path, rendering an uneven and potentially useless graft strip cross section. Further difficulty occurs when terminating the graft at the proximal end of the strip, and at the furthest distance from the skin incision near the knee. Without making a larger or second skin incision, this proximal cut may be performed somewhat blind, and therefore time-consuming and risking inadvertent tissue damage. Therefore, there is a need for an improved system and associated method that can consistently remove a target sized strip of tendon tissue from the native tendon, overcoming the issues disclosed herein.

SUMMARY

Described herein is a system including a plurality of devices for harvesting a tissue graft from surrounding tissue, such as a QT. Defining the entire QT as the native tissue, the system and methods described herein are configured to disconnect a portion or strip of this native tissue from itself. Before being harvested or disconnected, this portion or strip is continuous with and non-discernable from the native tissue. Stated in another way, the portion or strip disconnected by the herein disclosed system is originally continuously coupled to the native tissue, along the entire length of the resultant strip, including at least three side surfaces of the resultant strip. The systems that form the graft strip dissects a continuous length through the native tissue along the entire length of the resulting strip or portion. The shape of the resultant portion or strip is defined by the system disclosed herein and can be altered with differing dimensions and methods of use of the disclosed systems, and cutting tools. Contrary to this, a vessel-harvesting tool for example, disconnects a target vessel from surrounding connective tissue along its length that may include smaller vessels and other connective and fatty tissues that are not remaining native vessel. It follows therefore, that this example harvested strip of vessel tissue (the target vessel) is disconnected from a plurality of tissues that are different from the target native vessel; the target native vessel is not a removed portion of itself along its entire length of the harvested vessel. The target native vessel is discernable from the connective tissue around it. It is coupled along its length to a plurality of tissues, and these tissues are different in composition to the target native vessel. In addition, the vessel itself at least partially defines the shape and size of the harvesting tool or the harvested tissue. As a further example, a polyp removal device disconnects a polyp from a substrate tissue, the polyp and substrate tissue not being the same tissue, and the polyp only coupled to the substrate at a first end of the polyp. In addition, the polyp is discernable from the substrate tissue and a device that disconnects a polyp does not define the boundary of polyp removed. The entire polyp is removed, the polyp defining the boundary.

Disclosed herein is a system that may be used to form a graft strip from the native tendon. It includes a static retractor that is flexible for insertion through a small skin incision, and is self-supporting, once under the skin. Retractor is configured to allow instruments access into a working cavity along the tendon, and may include features for improving access to the tendon. For example, retractor may include a pocket to selectively engage a guide, and place the guide along the tendon. While installed within the retractor, the guide may be configured to guide a trajectory and depth of cut of a dual blade scalpel along the tendon, so as to forms lateral sides of the graft strip. The retractor may also provide access to a proximal end of the tendon, such that a proximal cutter may transect a proximal end of the graft.

Disclosed herein is a retractor that is self-supporting for holding open an anatomic space developed in a patient. The retractor may be configured to hold open an anatomic space adjacent a tendon such as the QT, the space configured for harvesting a tendon graft from a portion of native tendon. The retractor may define an elongate body, with a proximal end, a distal end, a roof that defines a curved surface and a floor that defines a planar surface for engaging a surface of the tendon or tissue adjacent thereto. The retractor may define an elongate working cavity extending from an open distal end. The roof may include at least one opening extending therethrough, defining boundaries of bilateral wings at a distal end of the elongate body. The retractor is configured to be elastically collapsed to insert though a relatively small incision through the skin and into the anatomic space. The retractor may elastically collapse from a first (neutral) configuration to a second configuration that is collapsed or has a smaller profile than the first configuration, by external forces on the bilateral wings body. Release of the external forces on the retractor is configured to relax the retractor towards the first configuration and hold the anatomic space open without external support.

In some example embodiments, the roof may include a roof relief at a proximal end of the elongate body, the roof relief defining a 360 degree bounded hole configured to add flexibility to the retractor and thereby further decrease the collapsed profile of the retractor in the second configuration. In some example embodiments, the floor planar surface includes an elongate opening therethrough, the opening having a lateral width sized to provide visibility and tool access to an entire tendon width. In some example embodiments, the retractor also includes a means of engaging a cutting guide and orienting the cutting guide along the working cavity. In this example, the means of engaging and orienting may orient a shaft of the cutting guide along the working cavity, parallel to a longitudinal axis of the elongate body. In this example, the means of engaging and orientating may include a pocket extending from a proximal end of the working cavity, for receiving a cutting guide end therein. In some example embodiments, the retractor may provide audible feedback upon correct engagement of the cutting guide within the pocket. In some example embodiments, the distal end of the retractor defines an entrance into the working cavity, for receiving a guide tool and a harvesting tool simultaneously therethrough.

Another example embodiment of a retractor that is self-supporting is disclosed herein. Retractor may hold open an anatomic space developed in a patient for harvesting a tendon. The retractor may include an elongate body formed of a flexible material and include a proximal end, a distal end, a longitudinal axis, a roof having a curved surface and a floor having a planar surface for engaging a surface of the tendon. The elongate body may define an elongate working cavity extending from an open distal end. The distal end may define bilateral wings having free distal most ends. These bilateral wings are configured to be pinched towards each other, to temporarily reduce a profile of the retractor for easier insertion through a skin incision. Release of the bilateral wings are configured to relax the wings away from each other such that the retractor tents the anatomic space open without external support.

In some example embodiments, the roof may include an elongate roof opening that defines a roof boundary of the bilateral wings. Pinching of the bilateral wings moves the bilateral wings towards each other and into the elongate roof opening. In some example embodiments, the retractor includes a roof relief at a proximal end, the roof relief defining a 360 degree bounded hole configured to further reduce a profile of the retractor during insertion through the skin incision. In some example embodiments, the floor includes an elongate opening therethrough defining a floor boundary of the bilateral wings. In some example embodiments, the retractor includes a pocket extending from a proximal end of the working cavity, for receiving a cutting guide end therein. The retractor may also include a tab opening, configured to engage with the cutting guide upon engagement of the cutting guide within the pocket, the tab opening configured to provide audible feedback upon engagement. In some example embodiments, the distal end defines an entrance into the working cavity, for receiving a guide tool and a harvesting tool simultaneously therein.

An example system for harvesting a tendon graft is also disclosed, including a retractor, a guide, and a harvesting tool. The retractor is self-supporting for holding open an anatomic space developed in a patient above the tendon. The retractor comprises a flexible elongate body including a proximal end, a distal end, a longitudinal axis, a roof that is curved and a floor having a planar surface for engaging a surface of the tendon. The retractor defines an elongate working cavity extending from an open distal end. The guide has a handle end, a working end and an elongate shaft extending therebetween. The guide is configured to assemble with the retractor and fix the guide shaft along the working cavity. The guide's working end may define a dissecting leading edge. The harvesting tool includes a handle end and a working end with an elongate shaft extending therebetween. The harvesting tool's working end including a blade edge for cutting into the tendon and a contoured surface for engaging and translating along the guide shaft while in the working cavity. The guide shaft and contoured surface are configured to limit the trajectory and translation extent of the harvesting tool along the tendon.

In some example systems, the retractor may include bilateral wings having free distal most ends. The bilateral wings may be flexed and pinched towards each other to reduce a profile of the retractor temporarily for insertion through a skin incision. Release of the bilateral wings are configured to relax the wings laterally away from each other and tent the anatomic space open without external support. The retractor may include a pocket extending from a proximal end of the working cavity, for receiving the guide's working end therein and thereby orienting the guide shaft along the working cavity. In some example systems, the retractor has a distal opening sized to receive both the guide and the harvesting tool simultaneously therethrough. Some example systems may also include a proximal cutter, configured to extend along the working cavity and transect a tendon graft.

BRIEF DESCRIPTION OF THE DRAWINGS

The disclosure will be more fully understood by reference to the detailed description, in conjunction with the following figures, wherein:

FIG. 7C illustrates the working end of the dual blade cutter relative to the retractor when in the proximal location along the tendon, in accordance with the disclosure;

FIG. 7D illustrates the blunt dissector and dual blade cutter relative to each other at the proximal end of travel of the dual blade cutter, with the retractor removed, in accordance with the disclosure;

FIG. 8C illustrates a longitudinal cross section view of a blade assembled to the proximal cutter, in accordance with the disclosure;

FIG. 8D illustrates an isometric view of a working end of the proximal cutter, with the blade assembled thereto, the cutter housing shown translucent for simplicity of understanding, in accordance with the disclosure;

FIG. 8E illustrates a side section view of a working end of the proximal cutter, with the blade assembled thereto, the cutter housing shown translucent for simplicity of understanding, in accordance with the disclosure;

FIG. 8F illustrates a side section view of a working end of the proximal cutter, with the blade assembled thereto, the cutter housing shown translucent for simplicity of understanding, and the blade retracted configuration in accordance with the disclosure;

DETAILED DESCRIPTION

Figure 1:
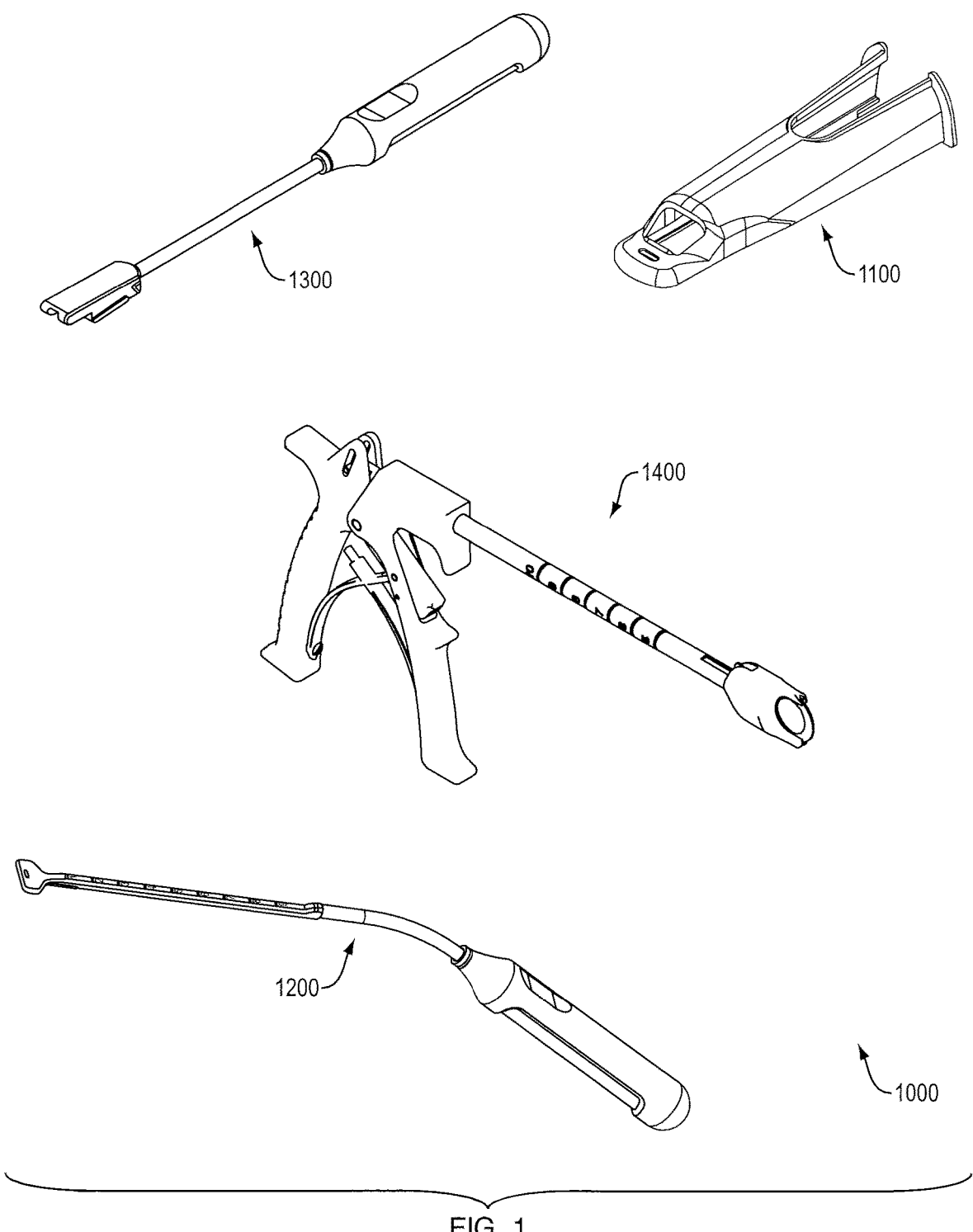
FIG. 1 illustrates an overview of an example tendon harvesting system of this disclosure.

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open-ended, include the listed parts and can include additional parts that are not listed. "And/or" is open-ended and includes one or more of the listed parts and combinations of the listed parts. Use of the terms "upper," "lower," "upwards," and the like is intended only to help in the clear description of the present disclosure and are not intended to limit the structure, positioning and/or operation of the disclosure in any manner.

Referring now to FIG. 1, an overview of an example system 1000 is illustrated, including a retractor 1100 and a plurality of instruments including but not limited to a blunt dissector 1200, dual blade scalpel 1300 and proximal cutter 1400. All or some parts of the disclosed system may be used, in combination with other instrumentation to harvest a tendon strip or graft from a native tendon. The system 1000 is configured to remove a strip of tendon tissue from the native tendon, consistently and reliably, according to the predetermined strip length, width and depth. The system 1000 may be configured to lie between the patient knee and a proximally disposed quadriceps muscle. As such, throughout this disclosure, the term "distal" relative to portions of the system define portions closer to the knee, and the term "proximal" define portions of the system that are closer to the patient thigh or quadriceps muscle. Stated in another way, the terms proximal and distal relate to the patient throughout this specification, rather than the tool use.

The system includes a retractor 1100 that is self-supporting and may be configured for insertion into a small incision near the knee. Retractor 1100 is preferably placed subcutaneously and along the surface of the Quadriceps Tendon, hereinafter "QT". The retractor preferably lies on the anterior surface of the QT. The retractor 1100 forms a working cavity for access to and visibility of the QT. Retractor 1100 is configured to provide access for the plurality of instruments of the system to the tendon via the working cavity. Retractor 1100 is configured to hold the working cavity open or tent the skin away from the tendon surface without requiring external forces, and is thereby self-supporting. External forces that are not required include for example a positioning arm or stand, a robot arm, or a second person with a paddle retractor. The retractor 1100 is configured to receive and/or operatively engage and guide the plurality of instruments, such as dissector 1200, harvester 1300 and proximal cutter 1400, while forming the strip of tendon tissue.

The blunt dissector 1200 may perform a plurality of functions, both independent of other portions of the system 1000, and while assembled thereto. For example, the blunt dissector 1200 may dissect the tissue before the retractor 1100 is inserted. Blunt dissector 1200 may also operatively couple to the retractor 1100 to provide a handle for retractor insertion and manipulation. Blunt dissector 1200 may also provide a trajectory guide to limit the trajectory of the harvester 1300. In some system embodiments, a separate tool may dissect the tissue first. The harvester 1300 may be configured to form two lateral sides of the tendon strip simultaneously, using portions of the retractor 1100 and blunt dissector 1200 as a guide to control the cut trajectory. The proximal cutter 1400 may slide along the retractor's working cavity and along a partially dissected tendon strip and disconnect the proximal end of the tendon strip from the native tendon.

Turning now to the details of the individual components of system 1000, and starting with the retractor 1100, a variety of views are illustrated in at least FIG. 2A-2J. Retractor 1100 may be a unibody or single molded element, formed of a flexible material. Retractor is configured to be collapsed, or reduced in profile and then inserted through an incision and under the skin. Once inserted, retractor 1100 is generally self-supporting and configured to hold open the anatomic space it is inserted into for performing minimally invasive surgical procedures. The retractor 1100 defines an elongate body, with proximal and distal ends, and may have a general arch shape or "C" shaped cross-section, defining a passage and longitudinal working cavity therealong. Retractor 1100 preferably includes a rounded, tapered or streamlined shape along its length to facilitate insertion along the dissected space anterior of the tendon, with minimized tissue trauma. Retractor 1100 proximal end 1110 may be enclosed, with a lower profile than distal end 1120. Retractor floor defines a planar lower surface 1118 along its length, to lie relatively flat on an anterior surface of the QT. The QT may not necessarily be perfectly flat, but is considered mostly planar along its length, to engage a substantial portion of the planer lower surface 1118. Retractor 1100 may be formed of a plastic, and may be translucent to facilitate better tissue visualization. In addition to being formed of a flexible material, retractor 1100 also includes a plurality of reliefs to improve elastic deformation of the retractor 1100, for easier insertion through the incision and under the skin. However, the retractor 1100 is sufficiently rigid to return towards its non-deformed shape once under the skin, and push the skin up to form a tent or working cavity. This provides the surgeon with a working cavity on the target tendon, the tendon readily visualized through the incision and open distal end 1120 of retractor 1100. Retractor 1100 may include flanges 1117a, 1117b extending radially from a distal end 1120 of retractor 1100. Flanges 1117a, 1117b may mirror images of each other, either side of the longitudinal axis of the retractor 1100 and may extend orthogonal to the longitudinal axis. Flanges 1117a, 1117b may maintain a location of retractor relative to the skin incision. Flanges 1117a, 1117b may remain external to and directly adjacent the skin incision when retractor 1100 is inserted. Flanges 1117a, 1117b may act as a stop, limiting insertion depth of the retractor 1100 into the anatomical space.

Retractor 1100 defines a proximal end 1110 that is tapered and a distal end 1120 defining an opening for a surgeon to have direct visualization of the target tendon and place instruments therethrough. Retractor 1100 may be of any length that is suitable for harvesting the QT, and may be generally between 3-5 inches long in its entirety, and define a working cavity having a cross sectional dimension "W" between 1-2 inches. Since the skin incision is as small as possible, preferably no wider than an inch, the retractor is configured to collapse and fit through this small incision and then pop open once inserted.

Retractor 1100 may define a shell body. Retractor 1100 may include a plurality of reliefs 1115 and 1116. A proximal relief 1115 may provide additional retractor flexibility while also providing an access window for an optional scope or light source. These optional instruments may extend through the skin directly adjacent relief 1115 and then through relief 1115. Relief 1115 may define a 360 degree (°) bounded hole, the boundary defined entirely by the retractor 1100. Relief 1115 may be oblong in shape having a longer opening dimension across the width of retractor 1100.

Figure 3:
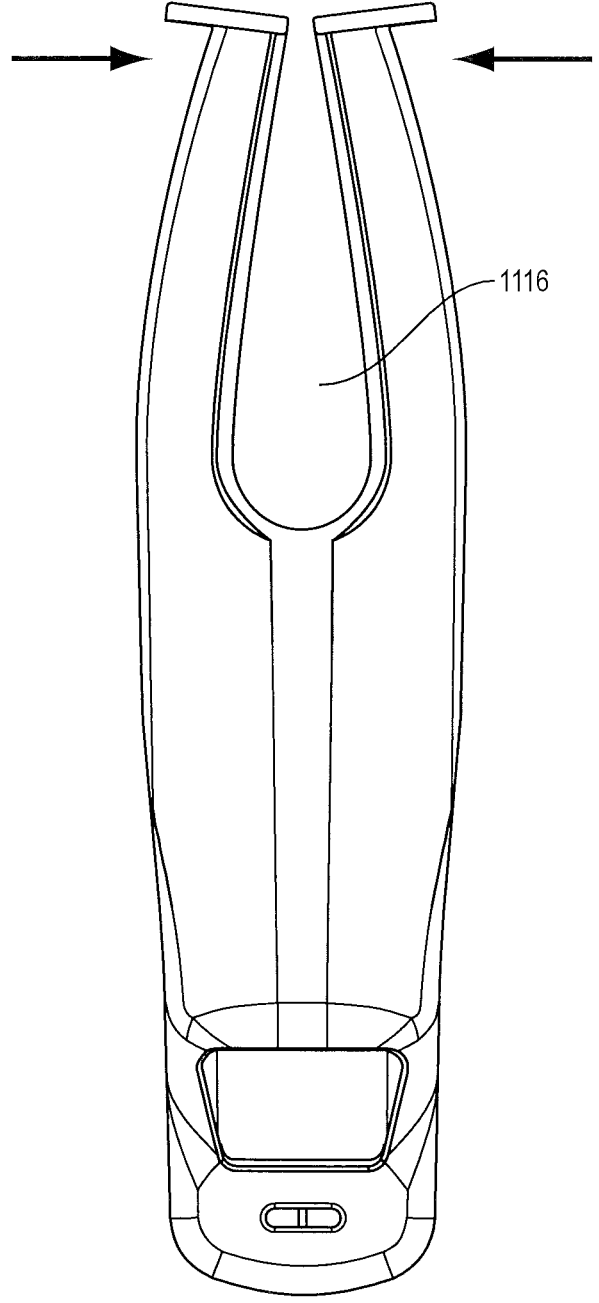
FIG. 3 illustrates a pinched or collapsed configuration of the retractor, in accordance with this disclosure.

Roof relief 1116 may extend from a distal end 1120 of retractor 1100, up to and including the distal most edge. Roof relief 1116 therefore defines a slot that has an open distal end. Roof relief 1116 may define a boundary with elongate ribs 1119 that extend around at least a portion of the boundary of relief 1116. Ribs 1119 may aid in further tenting the skin and may add some resilience to limit the skin from collapsing the retractor 1100 when inserted. Roof relief 1116 defines a medial boundary for bilateral wings 1112a, 1112b either side of the retractor 1100. Wings 1112a, 1112b may be squeezed or pinched together during insertion into the skin incision. As shown in FIG. 3, wings 1112a, 1112b are sufficiently flexible to touch or nearly touch for easy insertion through a relatively small incision. During pinching, the wings 1112a, 1112b move into the roof relief 1116 space.

Retractor has a cross sectional width W (FIG. 2E) that is preferable wider than the QT, to better identify surrounding structures. Retractor 1100 defines an upper curved roof portion 1124, bilateral sidewalls 1125a, 1125b (including the wings 1112a, 1112b), and bilateral stands 1126a, 1126b. The upper curved roof portion 1124 and bilateral sidewalls 1125a, 1125b are configured to lift or tent the skin. The bilateral stands 1126a, 1126b may define planar surfaces of the floor 1118 that may engage both the anterior surface of the QT and tissue lateral to the QT. For access to the anterior QT surface, bilateral stands 1126a and 1126b are laterally disposed and define an elongate medial opening 1130 along the retractor 1100. Bilateral stands 1126a and 1126b may define a smaller width opening (G2) towards the proximal end 1110. Small width opening G2 may be uniform along its entire length and may extend up to the proximal end of retractor 1100. This opening 1130 may limit a trajectory of a cutting tool along the retractor 1100 and thereby along the target tendon. Medial opening 1130 may extend from a distal-most edge of retractor 1100 and extend along a substantial portion of retractor length, best seen in at least FIGS. 2B and 2F. Medial opening 1130 may be bounded by straight edges 1131*a*, 1131*b*, that are parallel to retractor longitudinal axis L-L. Medial opening 1130 may by coextensive with relief 1115. Medial opening is configured to provide access for a harvester 1300 to the QT anterior surface.

Figure 2A:
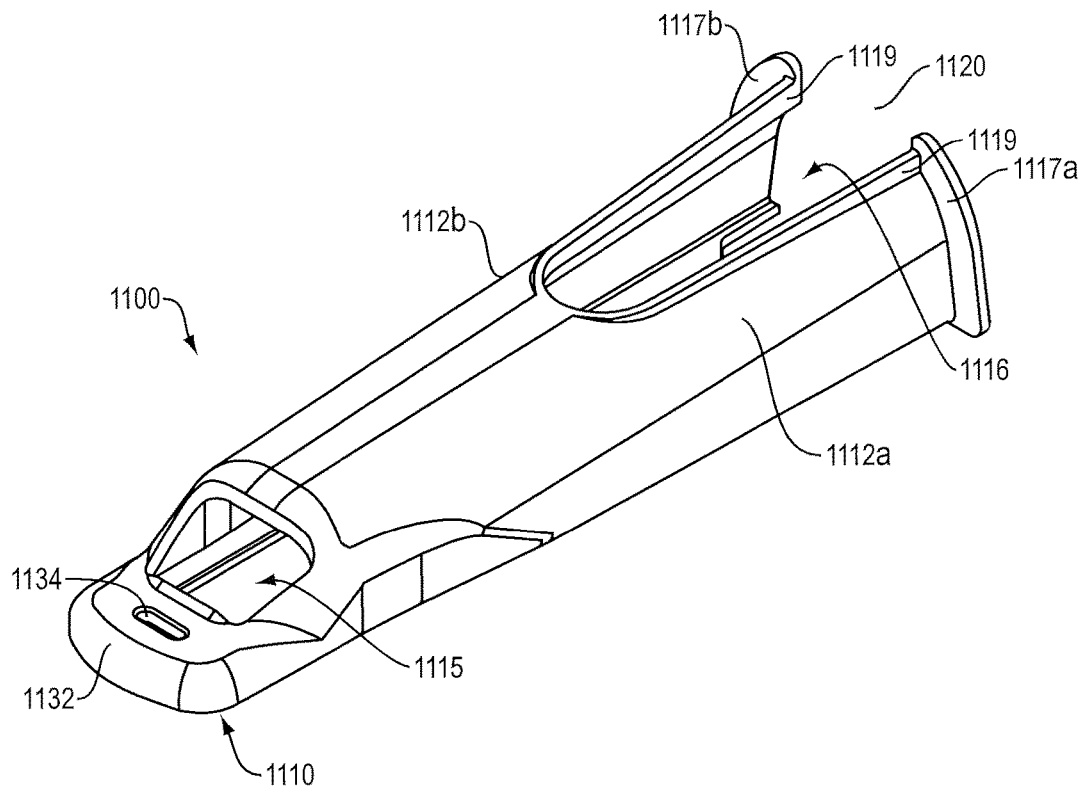
FIG. 2A illustrates an isometric view of a retractor, in accordance with this disclosure.
Figure 2B:
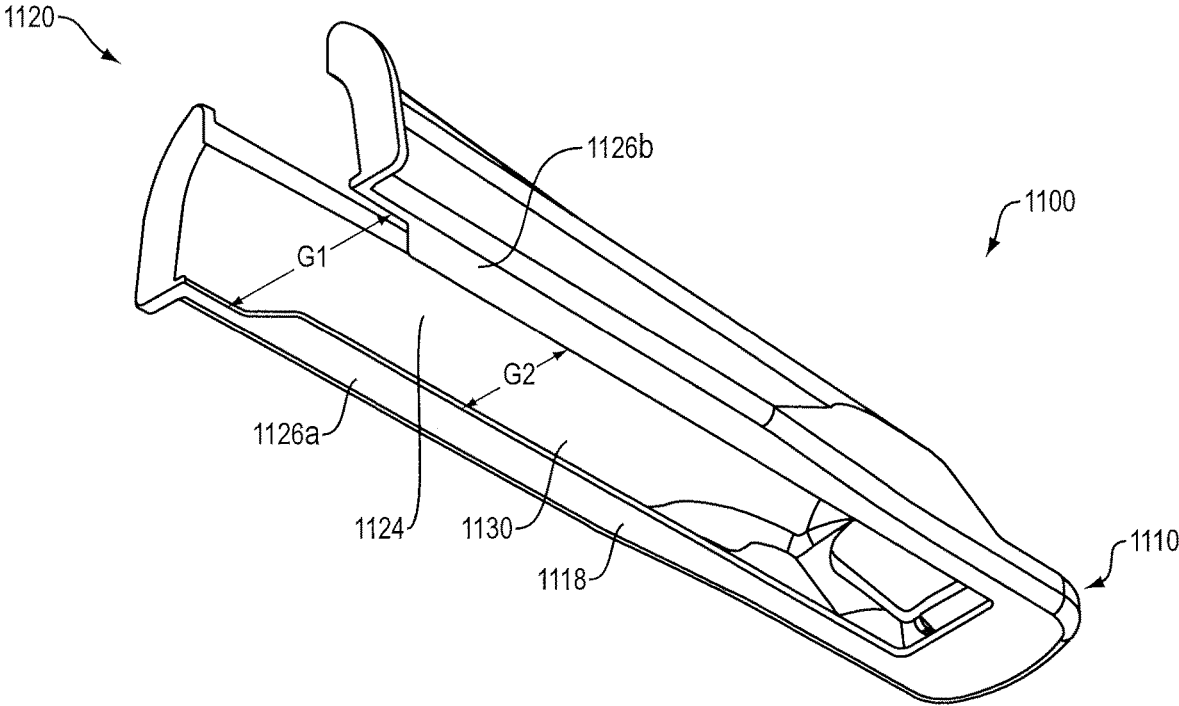
FIG. 2B illustrates an isometric view of a bottom side of the retractor, in accordance with this disclosure.
Figure 2C:
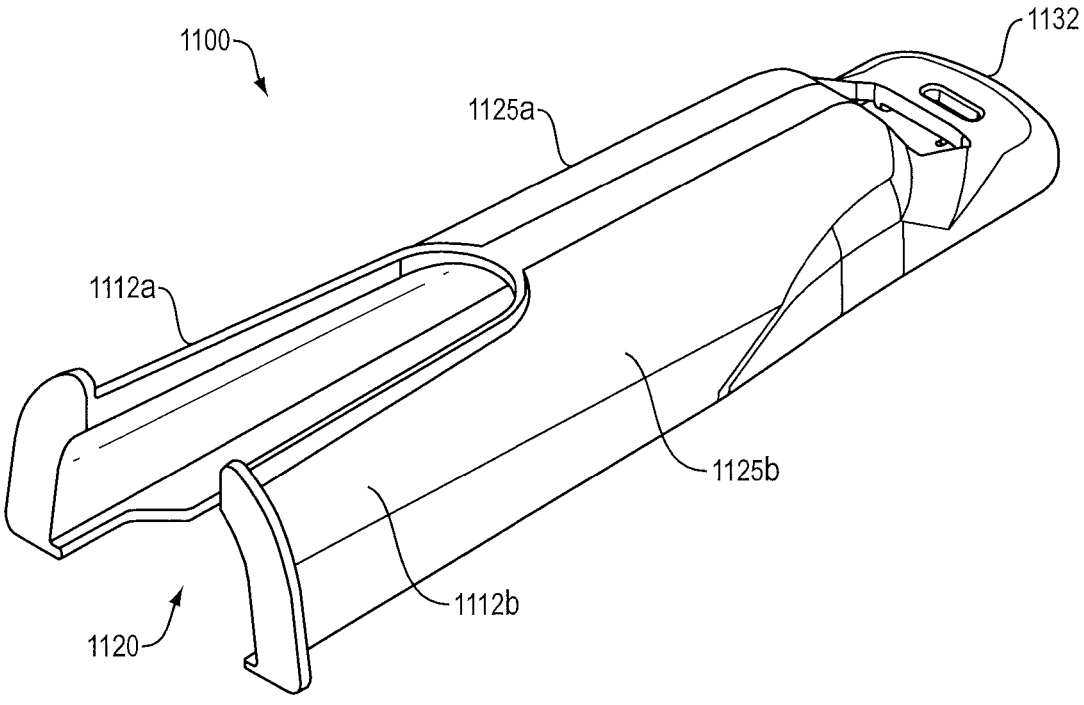
FIG. 2C illustrates an isometric view of a distal end of the retractor, in accordance with this disclosure.
Figure 2D:
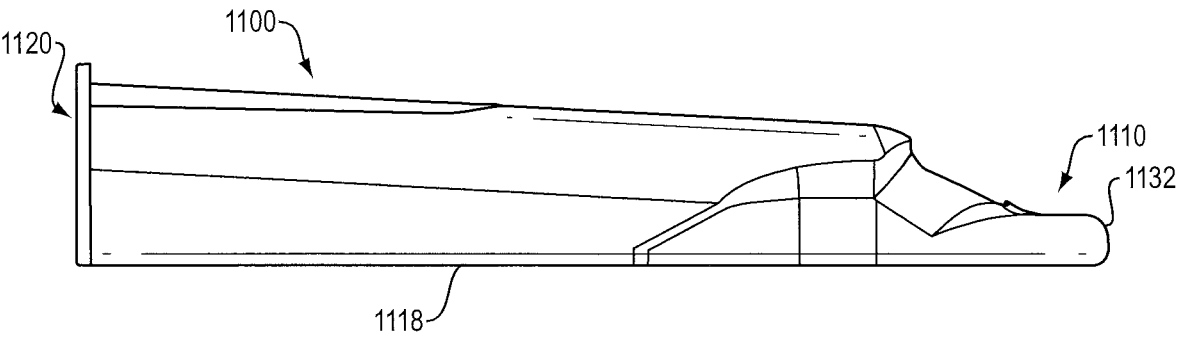
FIG. 2D illustrates a side view of the retractor, in accordance with this disclosure.
Figure 2E:
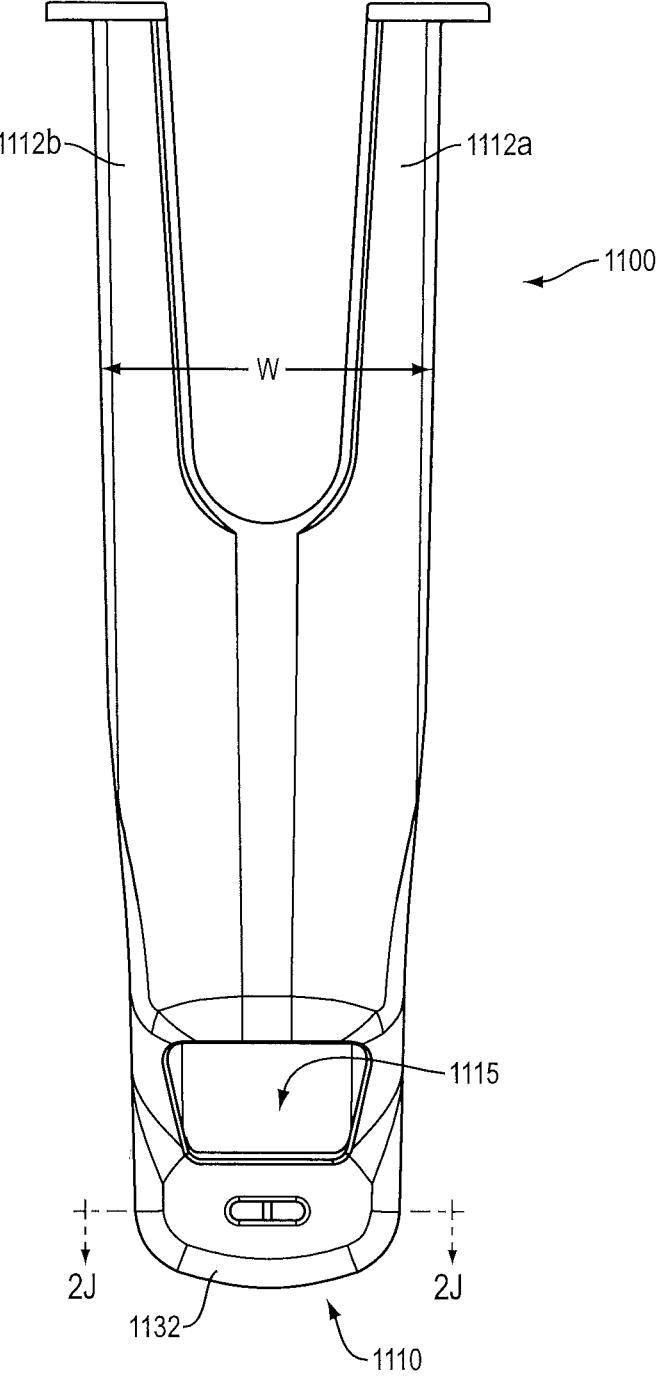
FIG. 2E illustrates a top view of the retractor, in accordance with this disclosure.
Figure 2F:
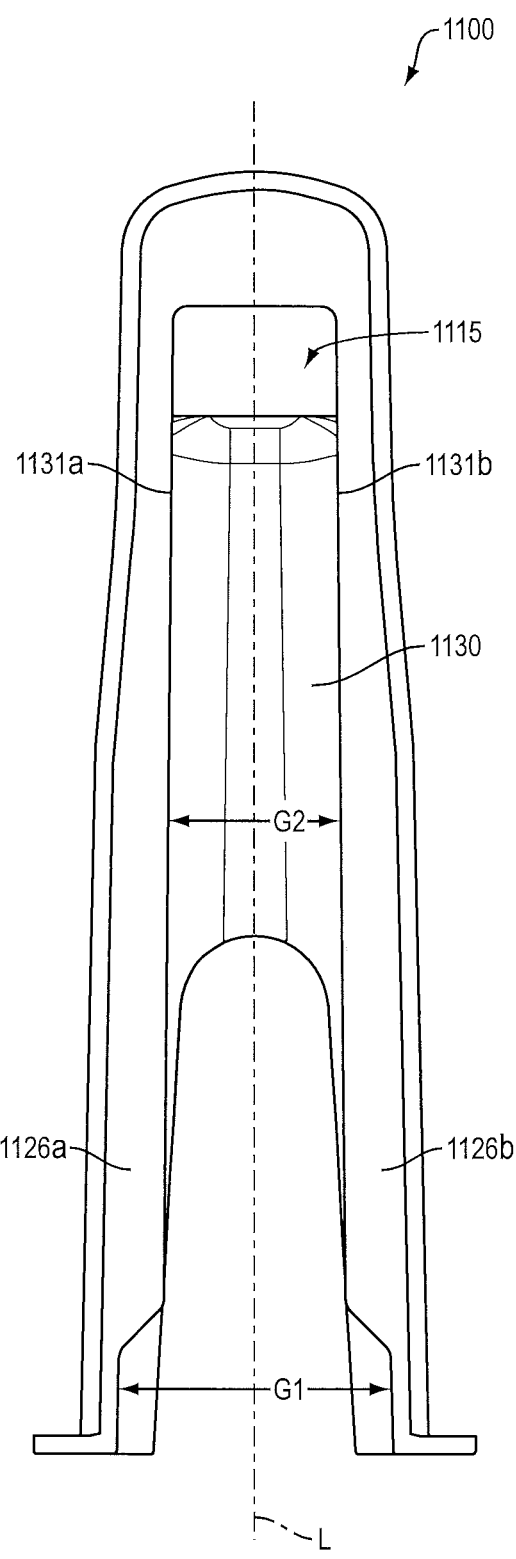
FIG. 2F illustrates a bottom view of the retractor, in accordance with this disclosure.
Figures 2G, 2H:
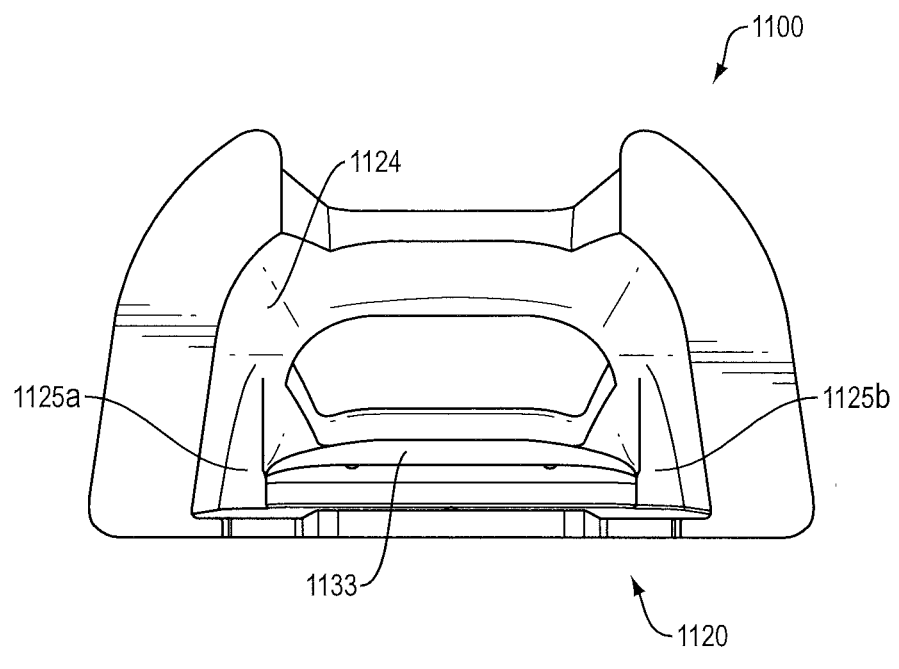
FIG. 2G illustrates a distal end view of the retractor, in accordance with this disclosure.
FIG. 2H illustrates a proximal end view of the retractor, in accordance with this disclosure.
Figure 2I:
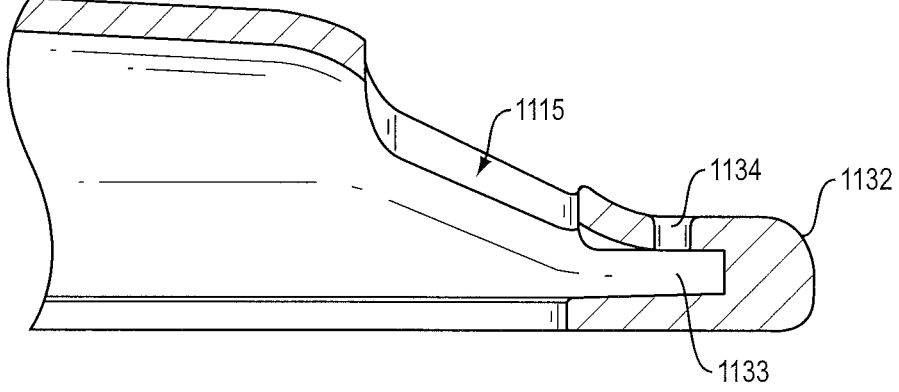
FIG. 2I illustrates a cross section of the proximal end of the retractor, in accordance with this disclosure.
Figure 2J:
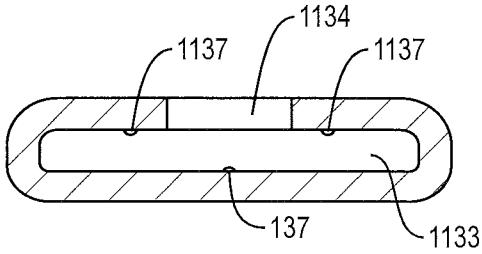
FIG. 2J illustrates a cross section of the proximal end of the retractor, in accordance with this disclosure.

Seen best in at least both FIGS. 2C, 2G and 2I, proximal end 1110 includes a nose 1132, extending proximally from relief 1115. Nose 1132 includes a pocket 1133 that is continuous with the working cavity. Pocket 1133 is configured to selectively operatively engage with a working end of a guide tool such as dissector 1200. In some embodiments, a guide tool may aid insertion and general handling of the retractor 1100. Guide tool may have a handle end, opposite the working end that extends along the retractor 1100 and out of retractor distal end 1120. Shown in FIGS. 5A and 5B pocket 1133 may operatively engage with a guide tool. Pocket 1133 may also include a means of positively engaging the example tool. Pocket 1133 may be sized to slideably receive guide tool working end, with a little clearance except for at a plurality of discrete locations, where crush ribs 1137 are located. FIG. 2J illustrates example locations of crush ribs 1137, that may extends along the longitudinal axis for a distance. Crush ribs 1137 are sized to locally reduce the pocket size and more positively engage a guides working end.

Figure 4A:
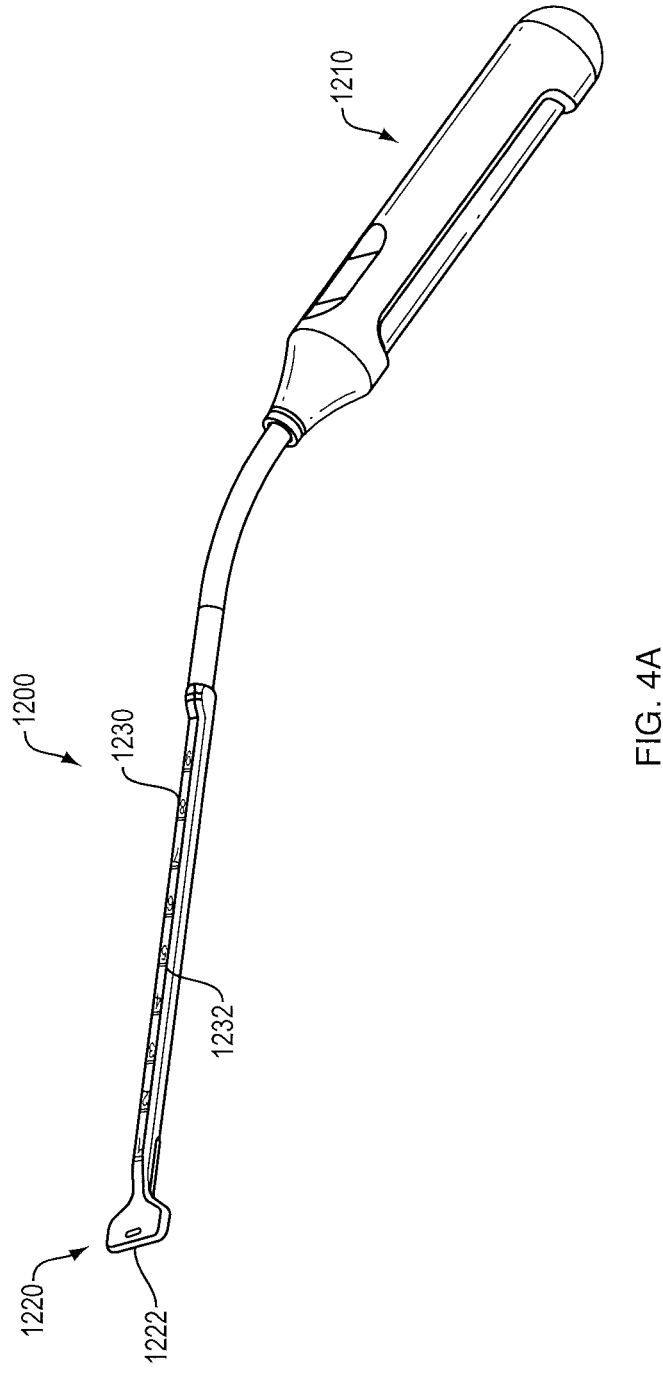
FIG. 4A illustrates an isometric view of a blunt dissector of this disclosure.
Figures 4B, 4C:
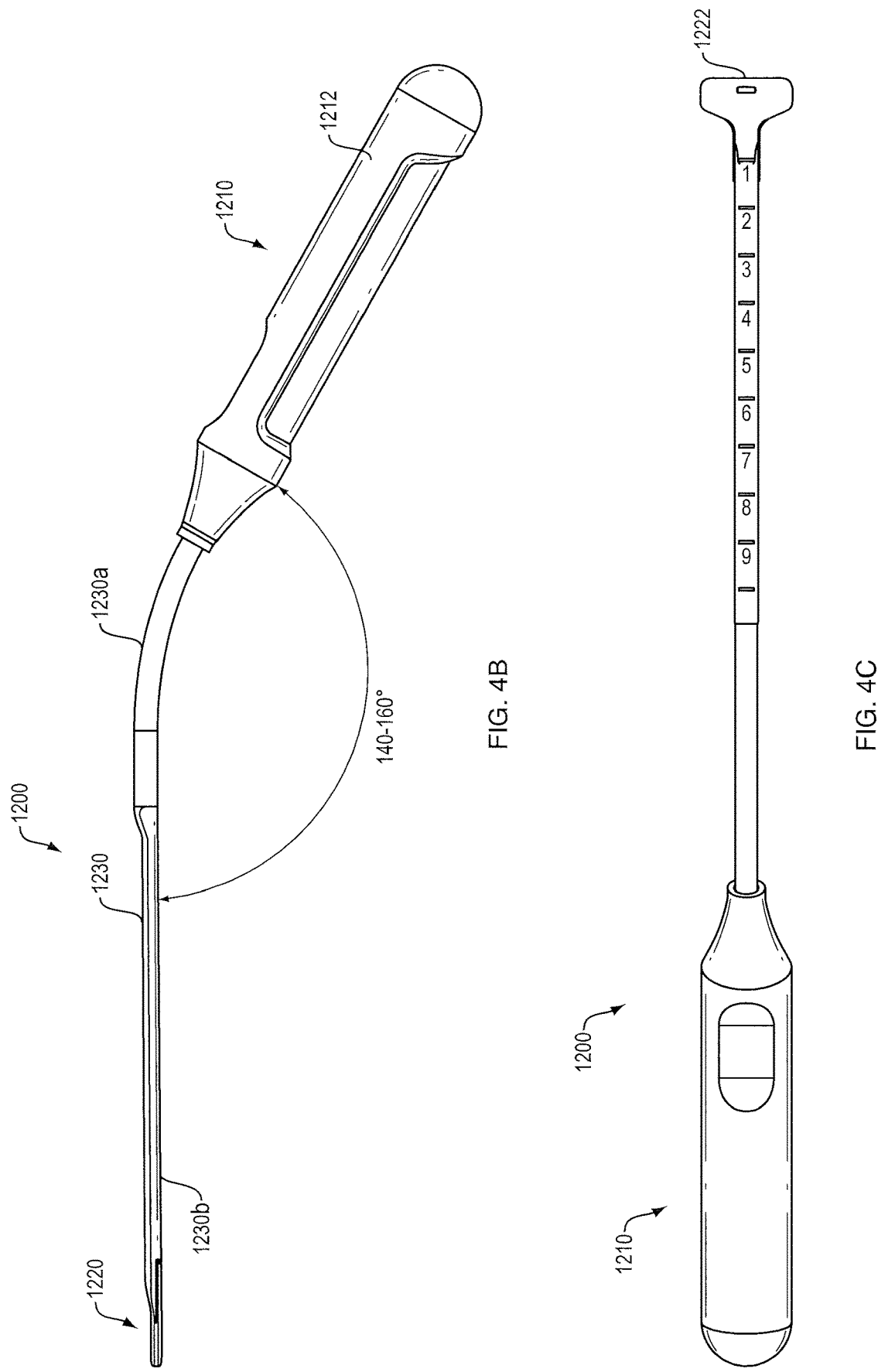
FIG. 4B illustrates a side view of the blunt dissector of this disclosure.
FIG. 4C illustrates a top view of the blunt dissector of this disclosure.
Figure 4D:
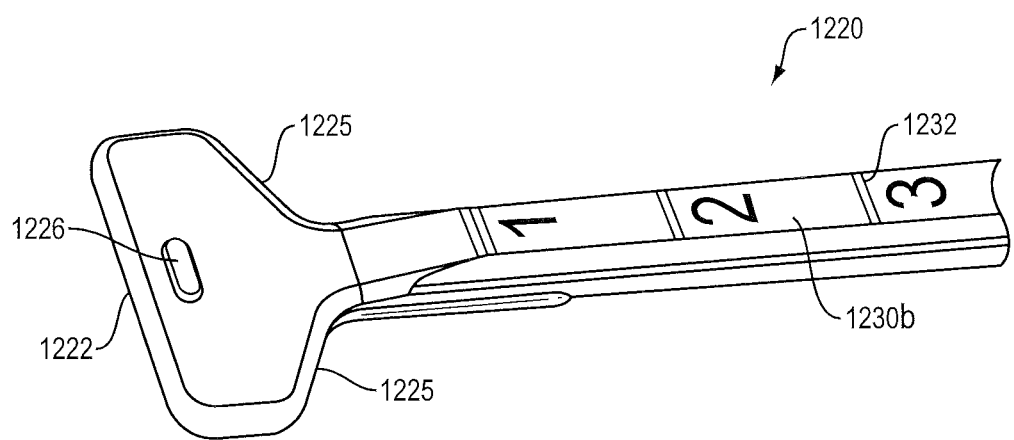
FIG. 4D illustrates a proximal end the blunt dissector of this disclosure.

Pocket 1133 may also include a means of providing positive audible feedback to the user that the guide tool is correctly engaged with pocket 1133. Aperture 1134 for example may click as a corresponding mating tab snaps therein and engages the aperture 1134. Blunt dissector 1200 may include a protruding key or tab, shown in at least FIG. 4A that is received by aperture 1134. Aperture 1134 may define an axis perpendicular to the retractor long axis. Aperture 1134 may, in combination with tab on dissector 1200, increase retention between the retractor 1100 and blunt dissector 1200. Audible feedback, or a clicking feel once correctly inserted may compensate for obscured visibility when engaging the guide tool (dissector 1200) while the retractor 1100 is already inserted. Since the guide tool (dissector 1200) defines a trajectory of a cutting tool into the tendon, the correct insertion of the guide tool is important. Removal of the dissector 1200 from the retractor 1100 may require deformation of the flexible retractor 1100 adjacent the aperture 1134 to remove the mating tab 1226 from the aperture 1134.

Details of the blunt dissector 1200 are illustrated in at least FIGS. 4A-4E. Blunt dissector 1200 generally includes a handle end 1210, working end 1220 and a shaft 1230 extending therebetween. Working end 1220 includes a leading edge 1222 that may be linear across its extent and is generally blunt, configured to separate tissue layers. Blunt dissector 1200 may be inserted through incision near the knee and advanced under the skin, to bluntly separate the skin layers from the anterior QT surface. As such, leading edge or dissecting edge 1222 is preferably not so sharp to cut or pierce tissue. It may however break through connective tissue connecting the QT anterior surface from the skin layers. Blunt dissector 1200 may be configured to clear away the fat pad under the skin. Blunt dissector 1200 may perform this separation before inserting the retractor 1100.

Handle end 1210 may be angularly offset from the working end 1220. Shaft 1230 may include a bend, forming the angular offset. Shaft 1230 defines a distal length portion 1230*a*, extending directly from handle 1212. Shaft distal length portion 1230*a* may define a first cross section that is circular. Angular offset may be formed along the distal length portion 1230*a*. Angular offset may be between 140-160 (°) degrees and is configured to align the shaft proximal portion 1230*b* along the tendon surface while angling the handle 1212 around a bent knee and out of the way. Shaft proximal length portion 1230*b* may be non-circular. Proximal length portion 1230*b* may define a straight linear length, configured to lie on or lie parallel to the relatively flat QT anterior surface. Proximal length portion cross section may include at least one planar surface 1233 that extends along the proximal length portion 1230*b*, on a top side thereof, seen best in FIG. 4E. In some embodiments, cross section defines an inverted "V" cross section or an inverted cropped "V". This cross section including the planar surface 1233 is configured to engage and guide a translation of a tendon-cutting tool, such as dual blade scalpel 1300, described in more detail later. Other possible configurations to guide and limit a trajectory of a cutting tool may include elongate slots or elongate rails along the dissector 1200 that operatively engage a mating feature of a cutting tool.

Proximal end of blunt dissector 1200 is shown in more detail in 4D. Shaft proximal length portion 1230*b* may include length indicators 1232 to indicate a length of QT or depth of insertion of the dissector 1200 along the QT. In some embodiments, working end 1220 may include indicators or markings (not shown) along the leading edge 1222, transverse the longitudinal axis of the shaft 1230 for estimating a width of tissue. Working end 1220 may be wider than shaft 1230, and may be termed a spatula. A tapered edge 1225 may extend between the shaft proximal length portion 1230*b* and leading edge 1222. Tapered edge 1225 may extend bilaterally from both sides of the shaft 1230 and, in some embodiments, may include a scalloped or cutting edge that may dissect connective tissue while retracting the blunt dissector 1200 (moving it distally). Tapered edge 1225 may also limit a trajectory extent of a cutting tool, as will be described later.

Figure 4E:
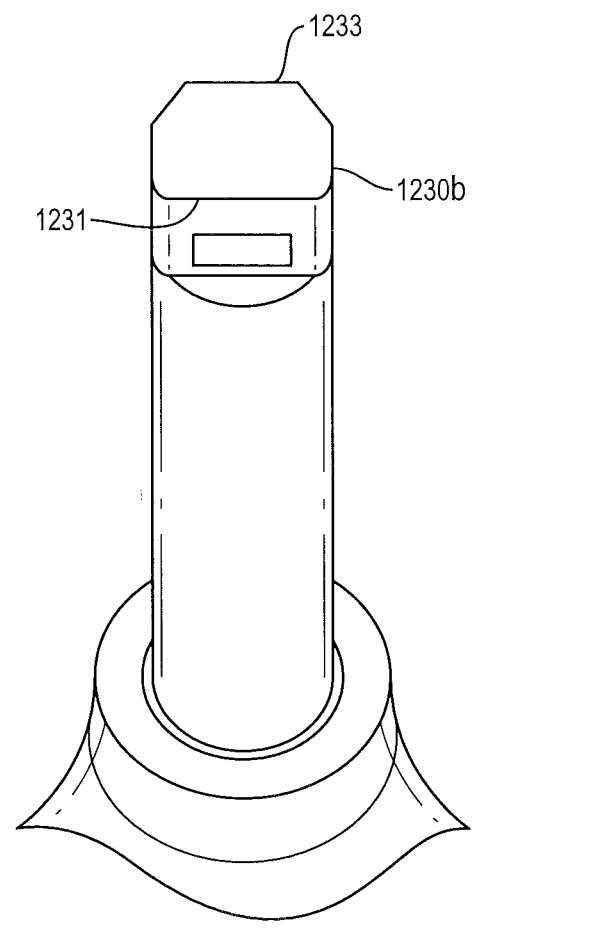
FIG. 4E illustrates a cross section of the blunt dissector shaft of this disclosure.

Top side of working end 1220 may include a tab or key 1226 to positively engage a mating feature of retractor 1100. Tab 1226 may be oblong and define a protruding element that inserts into aperture 1134. Tab 1226 may define a major length that is smaller than aperture 1134, allowing some lateral movement between the tab 1226 and aperture 1134, while limiting translation along the retractor longitudinal axis. FIG. 4E shows an example cross section of shaft proximal portion 1230*b*; including a lower side or surface 1231 that may be flat to engage the anterior surface of the QT. Superior surface 1233 is configured to engage and guide trajectory of a cutting tool, as will be explained hereinafter. Superior surface 1233 may be an inverted "V" or inverted cropped "V" and shaft portion 1230*b* may defining three surfaces angled relative to each other.

Figure 5A:
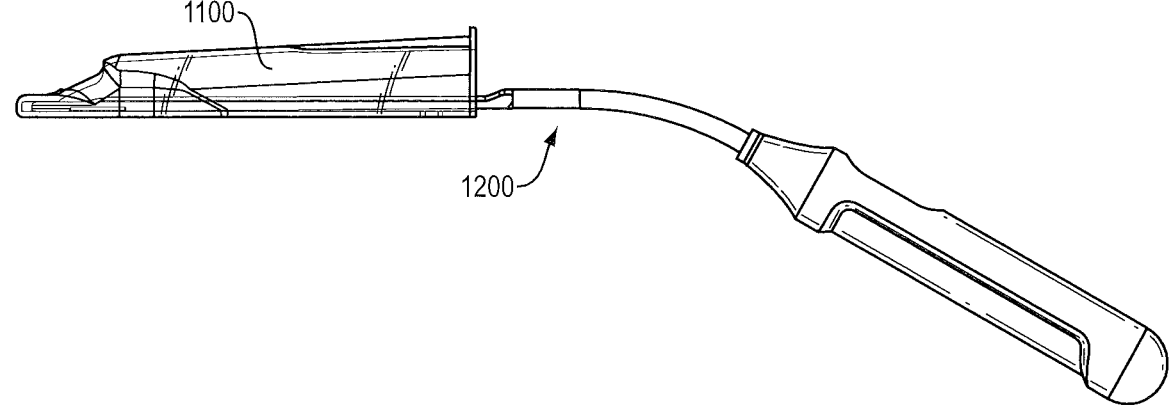
FIG. 5A illustrates a side view of the blunt dissector operatively coupled to the retractor, in accordance with this disclosure.
Figure 5B:
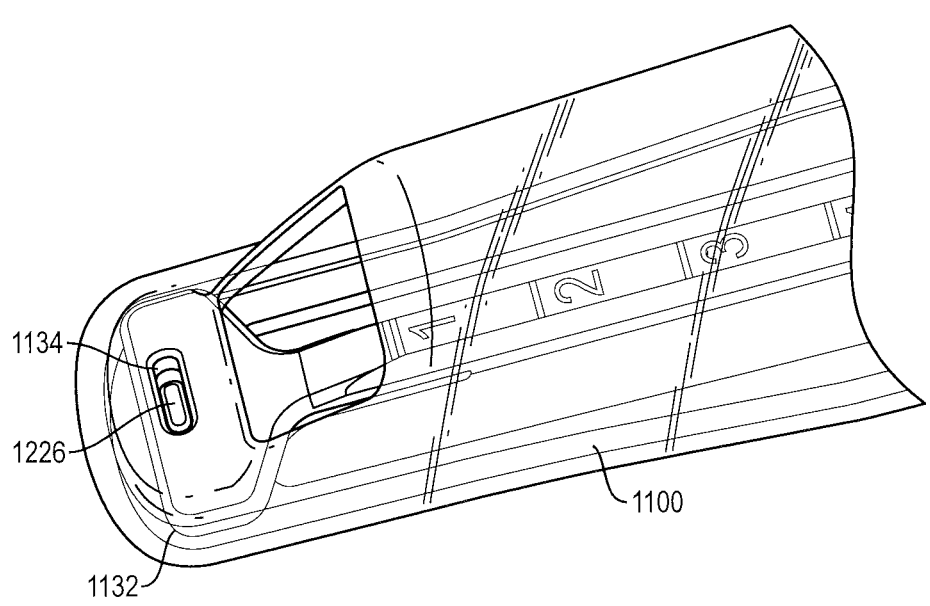
FIG. 5B illustrates an proximal end of the blunt dissector operatively coupled to the retractor, in accordance with this disclosure.
Figure 6A:
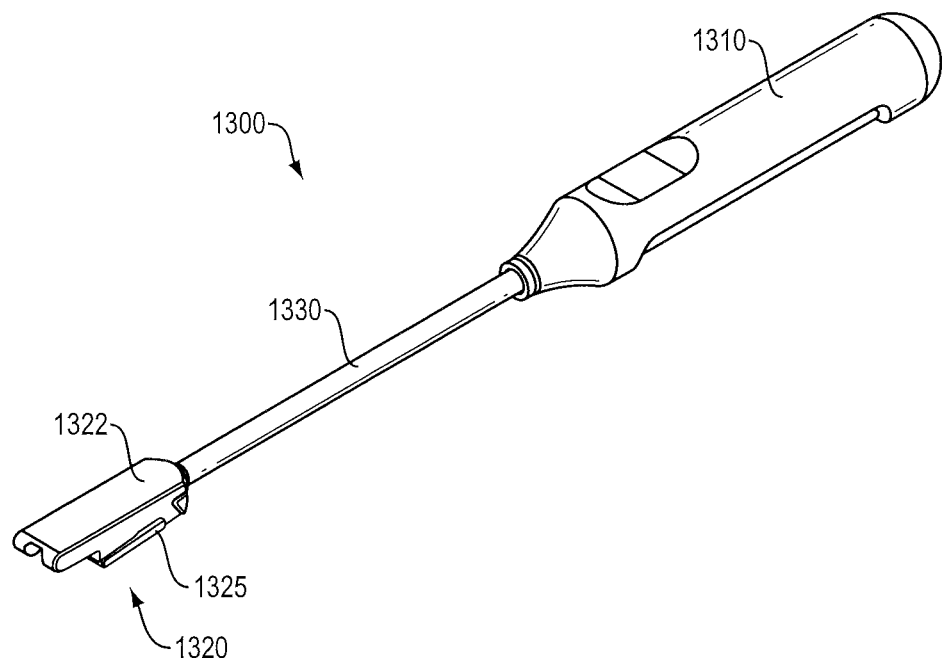
FIG. 6A illustrates an isometric view of a dual blade cutter of this disclosure.
Figure 6B:
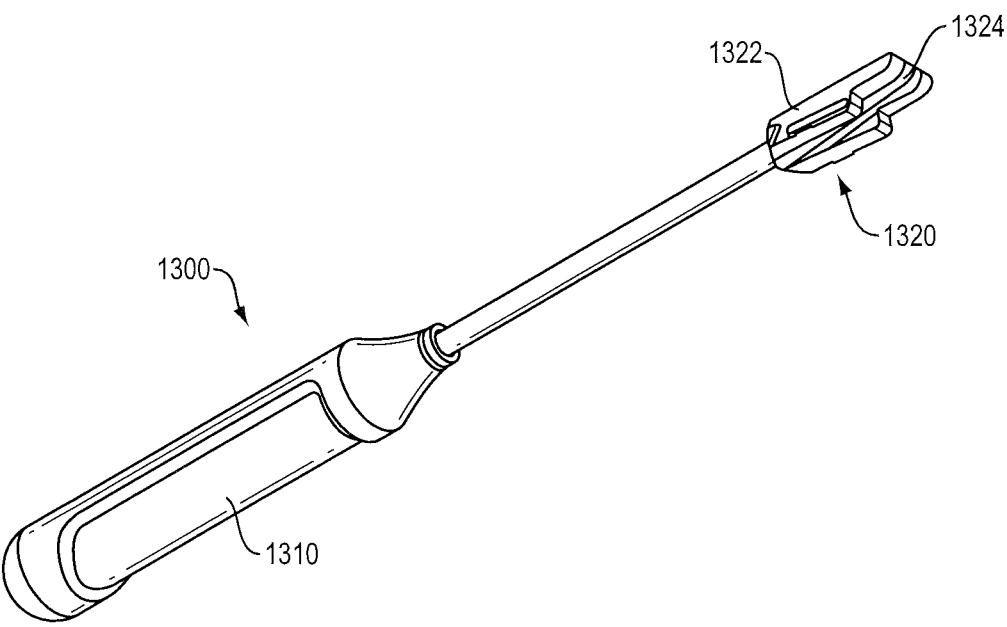
FIG. 6B illustrates a lower side isometric view of the dual blade cutter of this disclosure.
Figure 6C:
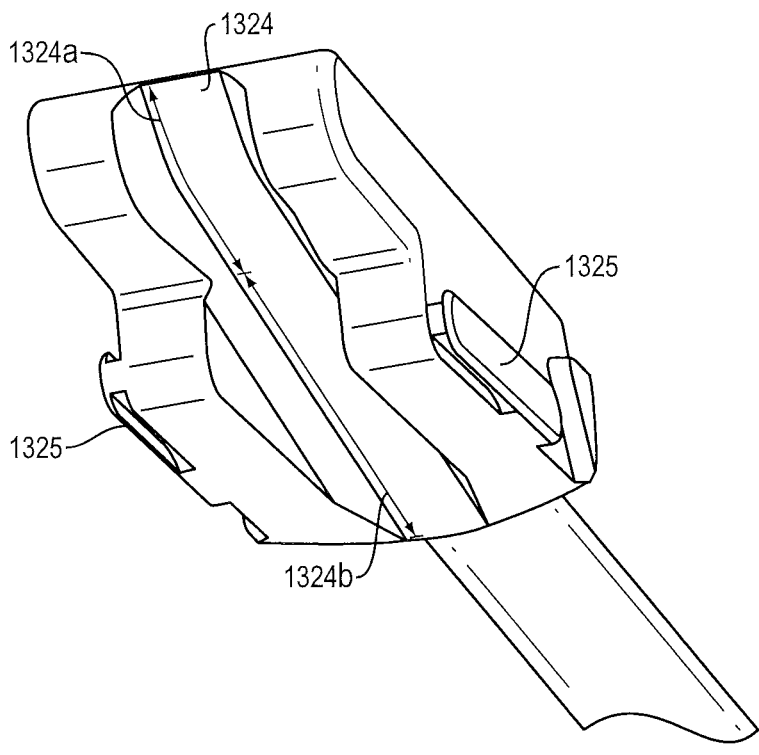
FIG. 6C illustrates a view of the working end of the dual blade cutter of this disclosure.
Figure 6D:
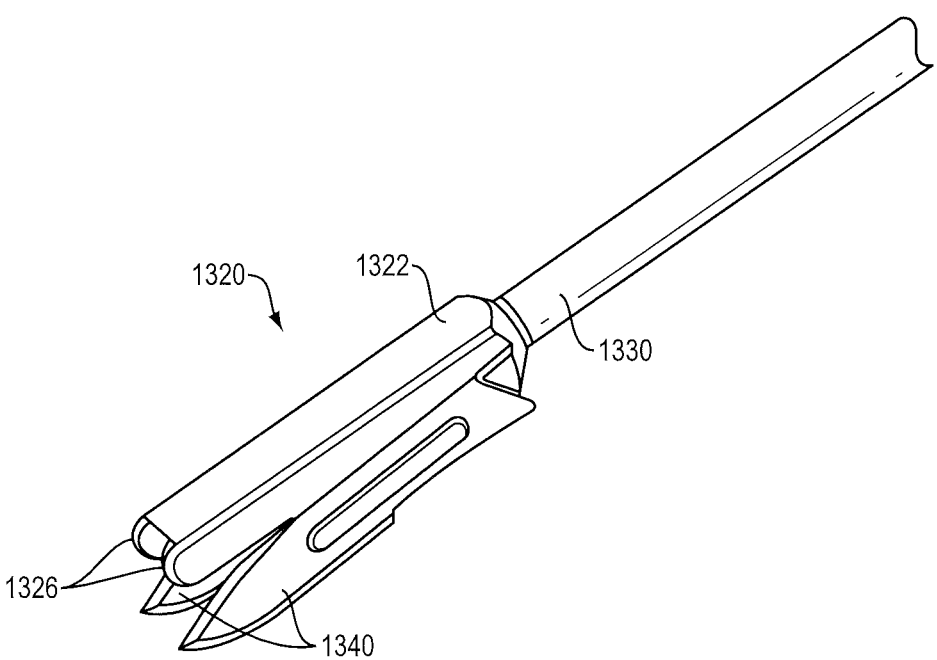
FIG. 6D illustrates a view of the working end of the dual blade cutter with the blades assembled, in accordance with this disclosure.

FIGS. 5A-5B illustrate various views of the dissector 1220 assembled with the retractor 1200, the retractor 1100 translucent in FIG. 5B for ease of understanding. Working end 1220 of blunt dissector may be selectively received by pocket 1133 of retractor 1100. Pocket 1133 may frictionally engage working end 1220. Pocket may include a plurality of discrete ribs 1137 to increase grip between the retractor 1100 and dissector 1200. Pocket 1133 may be sized relative to the working end 1220 such that retractor 1100 may deform or flex to receive working end 1220 therein. Pocket 1133 and blunt dissector 1200 may be coupled to aid insertion of retractor 1100 along the QT anterior surface. Alternatively, blunt dissector 1200 may be coupled once the retractor 1100 is inserted. When inserted along the QT anterior surface, lower surface 1231 may engage a portion the QT anterior surface and the shaft portion 1230*b* may align with longitudinal axis or retractor 1100 and preferably along a target cutting trajectory of the tendon. Blunt dissector 1200 may help in moving the retractor around while identifying the target cutting trajectory.

FIG. 6A-6D illustrates various views of a dual blade harvester 1300, configured to form two lateral sides of a resulting tendon strip 50' simultaneously, hereafter termed "Harvester". Relative to the patient, harvester 1300 forms two elongate cuts along the tendon 50, including a lateral and medial cut. Harvester 1300 includes a handle 1310 and working end 1320, with an elongate shaft 1330 therebetween. Shaft 1330 and handle 1310 may both extend along the same longitudinal axis. In other words, handle 1310 and shaft 1330 may not include any bend or angular offset, similar to the blunt dissector 1200. Handle 1310 and shaft 1330 may include reusable or multi use components, with a detachable working end 1320. In some embodiments, the working end 1320 is coupled to shaft 1330 via a release sleeve (not shown). In other embodiments, working end 1320 may define a housing 1322 fixedly coupled to shaft 1330 and include engagement means 1325 to selectively attach to blades 1340, illustrated in FIG. 6D. Engagement means 1325 may include elongate tabs, one each on lateral external surfaces of housing 1322. Engagement means may be oriented at an angle that defines a location of a leading cutting edge of blades 1340 and thereby depth of cut into the tendon. Blades 1340 may be standard scalpel blades. It is preferable that blades 1340 be single use and therefore consistently sharp for each procedure, as sterilization methods for reusable surgical tools tend to dull sharp edges. Harvester 1300 may be provided in varying configurations that may define selectable widths and depths of cut through and along the tendon. The different configurations may have differing widths and/or place the blades 1340 at differing angles to define the widths and depths of cut through and along the tendon. The two blades 1340 may preferably be parallel to each other, and form two equivalent cut depth into and along the QT simultaneously. Example lateral distances between blades 1340, defined by housing 1322 may be between 5-15 mm, and may more preferably be between 8-12 mm Turning now to FIGS. 6B and 6C, housing 1322 defines a lower surface that may include an elongate channel 1324, the channel having a cross section that receives and operatively slides with guide proximal shaft 1230*b* therein. Channel 1324 may define a cross section shape that may form a sliding fit with shaft 1230*b* of guide 1200, as illustrated in FIGS. 7D and 7E. Channel 1324 may mate and slide along mating surface 1233 of blunt dissector. The channel 1324 and blunt dissector shaft 1230*b* are configured to guide the trajectory and depth of cut of the harvester 1300 and thereby the blades 1340 along the retractor 1100 and into the tendon. The lower surface 1231 of blunt dissector 1200 may engage the tendon anterior surface. In other embodiments, only the retractor lower surface may engage the QT anterior surface. Depth D of cut may therefore be defined and controlled by the configuration of blades 1340, the working end 1320 and shaft 1230*b*.

Figure 7A:
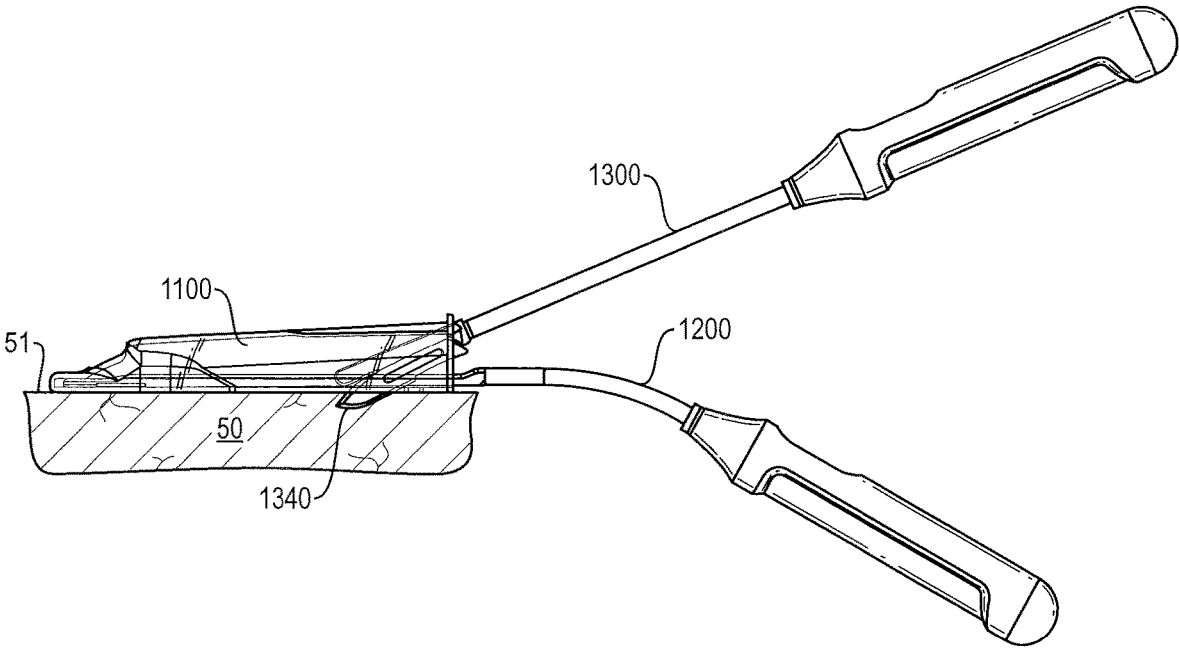
FIG. 7A illustrates a side view of the blunt dissector and dual blade cutter relative to each other and a tendon surface at a distal location along the tendon, in accordance with the disclosure.
Figure 7B:
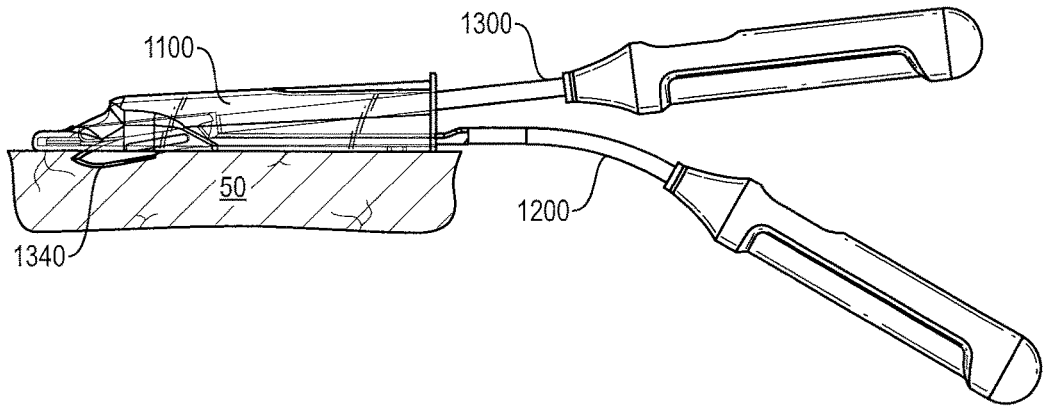
FIG. 7B illustrates a side view of the blunt dissector and dual blade cutter relative to each other and a tendon surface at a proximal location along the tendon, in accordance with the disclosure.
Figure 7E:
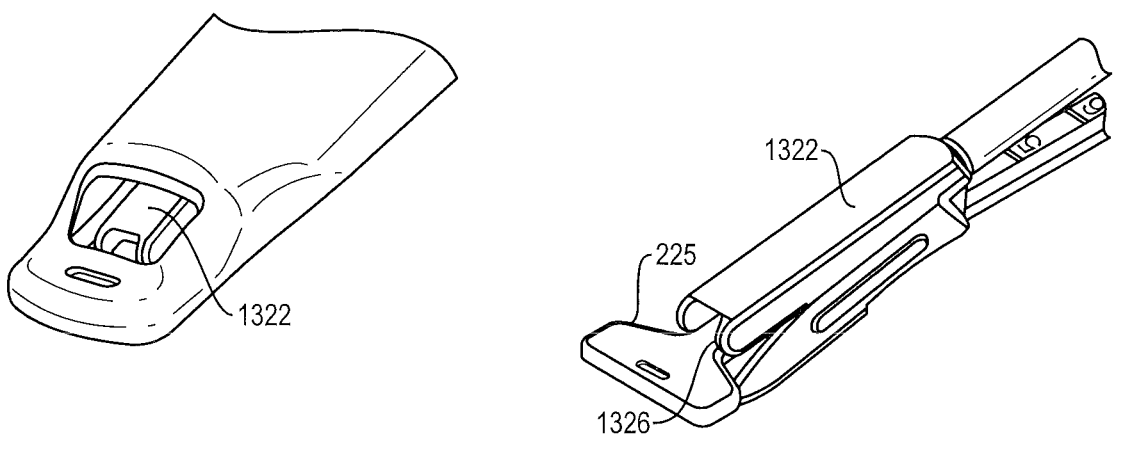
FIG. 7E illustrates a cross section view of the blunt dissector shaft and dual blade cutter shaft while cutting into the tendon tissue, in accordance with the disclosure.
Figure 7E:
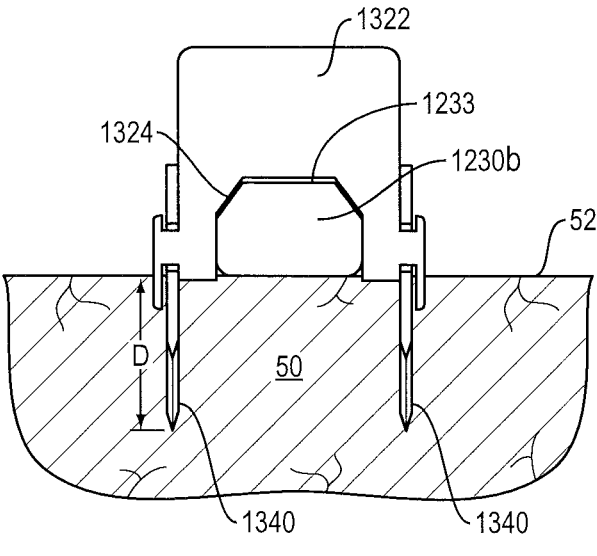

FIG. 7A illustrates the retractor 1100 placed on the tendon anterior surface 51, with the dissector 1200 assembled and inserted into retractor pocket 1133 and the harvester 1300 entering the retractor distal end 1110 and cutting into the tendon 50. FIG. 7B illustrates the harvester 1300 after translation along the tendon 50, at a proximal end of the retractor 1100. FIG. 7C illustrates a view of retractor proximal end 1110 with housing 1322 visible through relief 1115. FIG. 7D illustrates the harvester 1300 and dissector 1200 in a position similar to the shown in both FIGS. 7B and 7C, with the retractor 1100 removed for simplicity of understanding. In this location, blunt dissector 1200 may abut a surface of the harvester 1300 to limit the extent of this trajectory, thus proximally limiting the harvester translation. Tapered edge 1225 of dissector 1200 for example may be configured to limit the trajectory of harvester 1300, by abutting a distal surface 1326 and thereby blocking further translation. In other embodiments, a surface of the retractor may limit translation of harvester 1300.

Figure 7F:
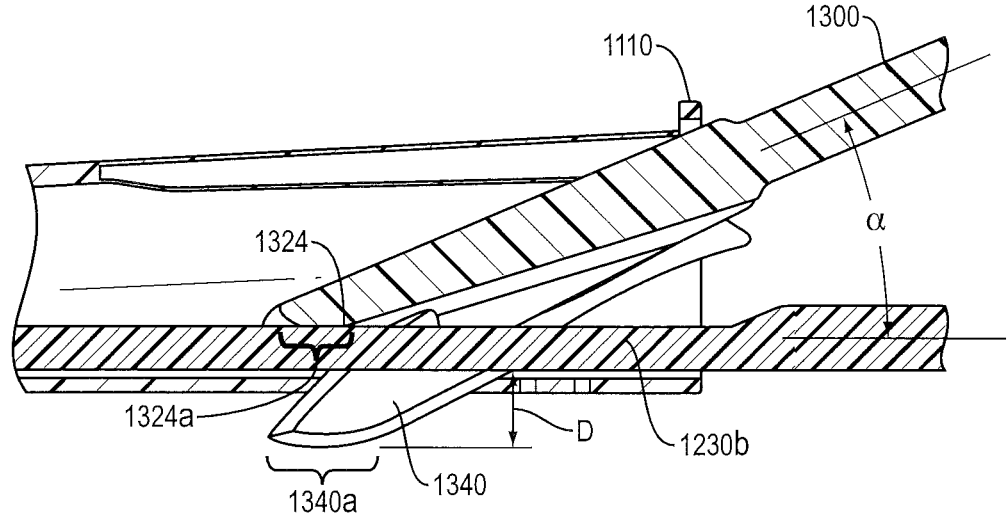
FIG. 7F illustrates a longitudinal cross section view of the blunt dissector shaft and dual blade cutter shaft, in the position illustrated in FIG. 7A.
Figure 7G:
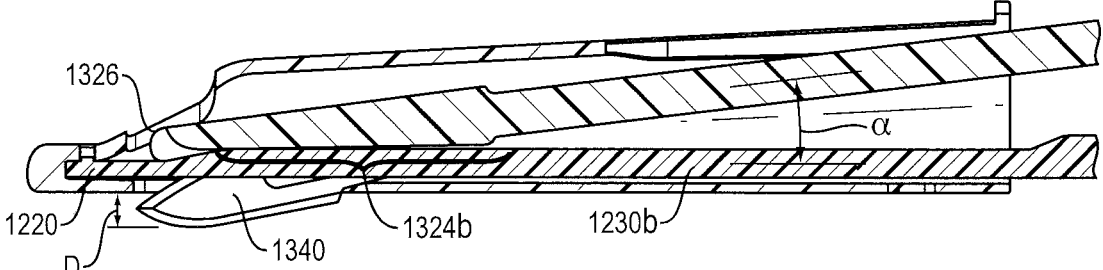
FIG. 7G illustrates a longitudinal cross section view of the blunt dissector shaft and dual blade cutter shaft, in the position illustrated in FIG. 7B.

FIG. 7F illustrate a cross section of the harvester 1300 engaging the dissector 1200 in a first position corresponding to FIG. 7A. Harvester 1300 may be at a distal end 1110 of retractor. FIG. 7G illustrate a cross section of the harvester 1300 engaging the dissector 1200 in a second position corresponding to FIG. 7B where the harvester 1300 has translated along the guide 1200 towards the proximal end of retractor 1100. Comparing FIG. 7F with FIG. 7G, it can be seen that the harvester angle $\alpha$ reduces as the harvester 1300 translates further into the retractor's working cavity. Channel 1324 is preferable contoured along its longitudinal axis to at least partially compensate for the changing angles of approach and maintain a substantially contact cut depth. For example, in the first position, the harvester is orientated at a larger angle of approach (angle $\alpha$) relative to the shaft 1230 and tendon anterior surface 51. A proximal contoured surface portion 1324*a* of channel 1324 (shown in FIG. 6C) engages the dissector shaft 1230*b*. Contoured surface portion 1324*a* may define a convex curved surface, coextensive with blade leading edge 1340*a*. In the second position, the harvester 1300 is orientated at a shallower angle of approach (angle $\alpha$) and a distal contoured surface portion 1324*b* of channel 1324 engages the dissector shaft 1230*b*. Contoured surface portion 1324*b* may define a linear surface, axially spaced and distal from blade leading edge 1340*a*. Contoured surface portions 1324*a* and 1324*b* define a cutting depth "D" that is the same, despite the variation in the angle of approach, provided the contoured surface portions engage the surface 1233 of dissector 1200.

The system 1000 may also include a proximal cutter 1400, configured to separate a proximal end of tendon strip from native tendon 50, details of which are shown in at least FIG. 8A-8E. This cutting operation occurs furthest from the skin incision making reliable cuts in the target area more difficult to achieve. Without the proximal cutter 1400, this cut end may be an uneven, jagged end, frustrating later suturing and coupling techniques. Proximal cutter 1400 forms a clean and uniform cut end, which makes later handling of the tendon graft easier. Proximal cutter 1400 includes a replaceable blade 1410 that is selectively operatively coupleable to a distal end of proximal cutter shaft 1440. Having a fresh blade 1410 for each procedure ensures a consistent sharp edge and a more consistent and precise uniform slice through the fibrous tendon tissue. Sterilization methods of reusable instrument may tend to dull sharp edges.

Proximal cutter 1400 includes a handle end 1430 and a guillotine style cutter at a working end 1450 of the cutter 1400. A shaft 1440 extends between the working end 1450 and handle end 1430. Shaft 1440 may include length estimation markers therealong and may include a static outer shaft and axially moveable inner pull rod 1436, which may be coaxially disposed along outer shaft. A blade housing 1452 may extend from shaft 1440. Blade housing 1452 may bilaterally extend from shaft 1440, the shaft longitudinal axis centrally disposed relative to the blade housing 1452. Blade housing 1452 may define a longitudinal axis that is coincident with and parallel to a shaft longitudinal axis. Stated in another way, blade housing 1452 longitudinal axis is preferably not angularly offset from shaft longitudinal axis.

Blade 1410 defines a generally thin planar element with a connecting end 1414 and cutting end 1415 extending therefrom. Cutting end 1415 includes an aperture 1412 configured to receive a strip of tendon therethrough. Aperture 1412 may define a 360 degree (°) bounded opening, with curved edges. Aperture 1412 may be oblong and sized to receive a tendon strip that includes a bone block therethough. Aperture 1412 may therefore define a cross section larger than the target graft strip width or cross section, as the bone block may be slightly larger and more rigid than the graft strip. This is termed a full thickness graft. Aperture 1412 may have an effective diameter configured to receive a graft and bone block up to 12 mm. Aperture boundary may define an arc length 1412a that is sharp. Arc length 1412a may be transition to a less sharp arc length 1412b. Arc lengths 1412a and 1412b may generally face each other, with the sharp arc length 1412a along a furthest edge from handle 1430, defining a proximal side of the aperture 1412. In operation, a tendon strip is slid through aperture 1412 and the working end 1450 is slid along the tendon strip to a prepared tendon strip proximal end. Tension on the tendon strip while positioning the working end 1450 tends to slide the tendon strip along a distal edge or arc length 1412b of aperture 1412. There may be some weaker tissue bridges forming some snagging discrete connections between a posterior surface of the tendon strip and anterior surface of remaining native tendon. Therefore, while arc length 1412b may be preferably less sharp than 1412a to avoid any unintended damage to the graft strip while placing the working end 1450 at a strip proximal end, the distal side of aperture 1412b may be configured to break these snagging tissue bridges is preferable. Arc length 1412b may therefore have some sharpness, sufficient to break these tissue bridges along the tendon while advancing the cutter 1400.

Housing 1452 defines a slot 1454 extending through the housing longitudinal axis, for receiving the blade's connecting end 1414 therethough. Blade connecting end 1414 extends through to a distal or handle side of the housing 1452 to couple to pull rod 1436. Housing 1452 may include a curved leading edge 1456 that may be sharp to cooperate with blade 1410 while transecting the tendon strip. Leading edge 1456 may also aid in breaking snagging tissue bridges while advancing the proximal cutter 1400 along the strip 50', in combination with aperture arc length 1412b. Housing 1452 includes a lead-in to slot 1454 to receive the blade 1410 therein. Slot leading edge may be asymmetric, seen best in FIG. 8E, having a first distal edge surface 1453 on a first side of the slot that is disposed on a first side of the blade 1410 that is tapered and axially spaced from a second distal edge surface 1455. Second distal edge surface 1455 is disposed on a second opposing side of the blade 1410 and may extend further along blade 1410. This offset in distal edge surfaces (1453, 1455) forms a lead in for the blade 1410.

Housing 1452 includes an arced opening defined at least partially be edge 1456 that may approximately match aperture 1412 in size and shape. In operation, cutter 1400 has two configurations. A first configuration shown in FIG. 8D, defining an open configuration, for receiving the tendon strip through aperture 1412 When in the target location, retraction of the blade 1410 may move the blade distally, towards the handle and into the housing 1452 to transect the tendon strip. In this second or cut configuration the aperture, 1412 is preferably reduced to beyond zero, such that arc length 1412a may be recessed or covered by housing 1452.

Actuation of the handle 1430 retracts blade 1410 to cut the tendon tissue. Handle 1430 may include two levers 1432a, 1432b pivotally coupled to each other and may include at least one biasing member 1434 therebetween. Lever 1432a may be fixed or static. Lever 1432b may be operatively coupled to a first end of pull rod 1436 and activation (motion) of lever 1432b may axially retract pull rod 1436 and thereby retract blade 1410. Handle 1430 may define a pistol grip handle 1430. Lever 1432b may include a slot 1433 that receives a pull rod pin 1427 therethough, such that rotation of lever 1432b towards lever 1432a slides pin 1437 and retracts pull rod 1436. Release of actuation forces on lever 1432b may spring lever 1432b back, to move the blade 1410 to the open configuration, courtesy of biasing member 1434. Other mechanical constructs are contemplated by the inventors, known in the art that may retract a pull rod. In other embodiments, either or both lever arm may move relative to each other. Activation of handle is configured to move the blade 1410 from a position that may receive the tendon therethrough to a position that covers the entire blade aperture 1412 with housing 1452. Therefore, in some example embodiments, housing 1452 may move and the blade 1410 may be stationary. In other embodiments, both the housing 1452 and blade 1410 may move towards each other.

Figure 8A:
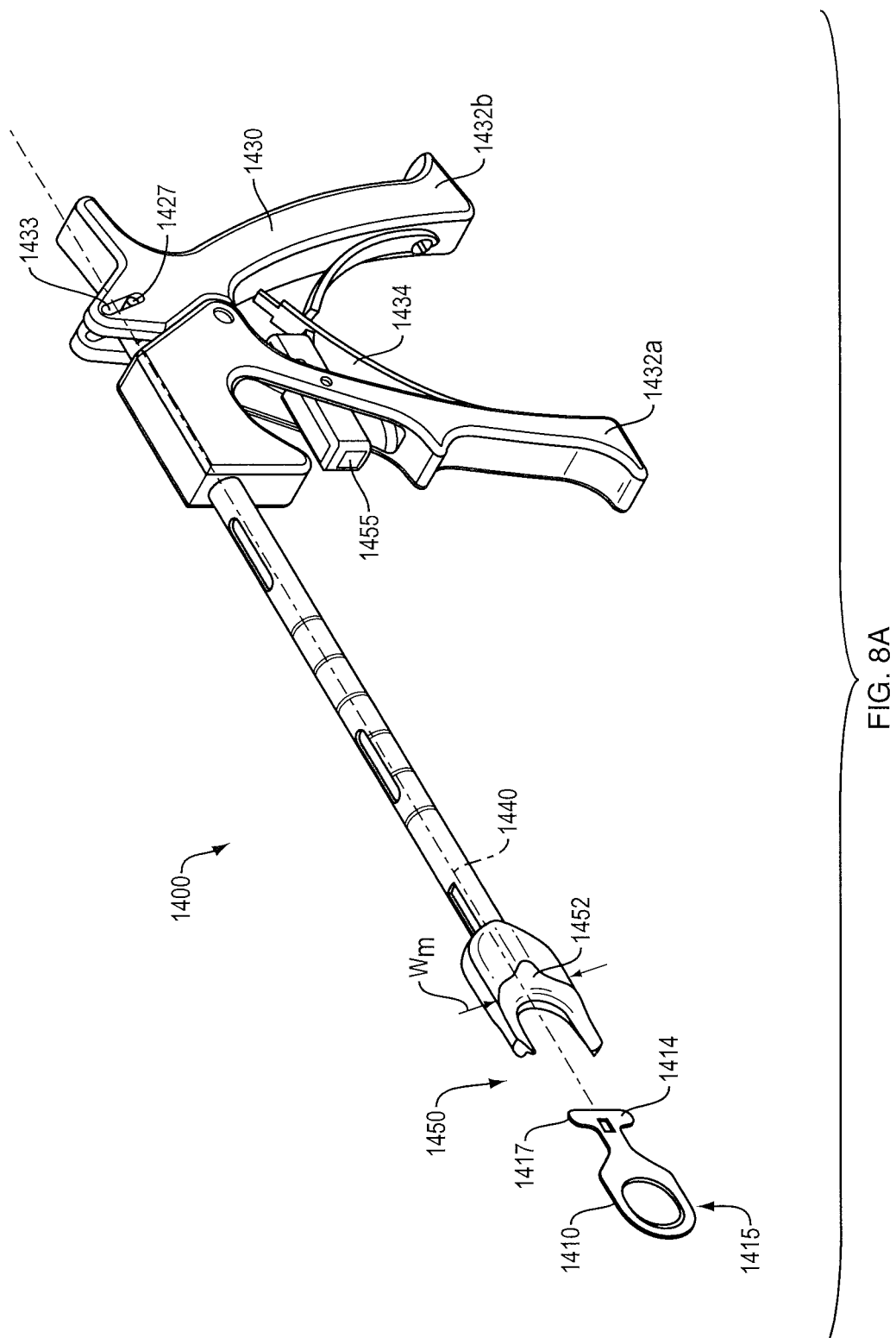
FIG. 8A illustrates an isometric view of a proximal cutter with the blade shown in exploded form, in accordance with the disclosure.
Figure 8B:
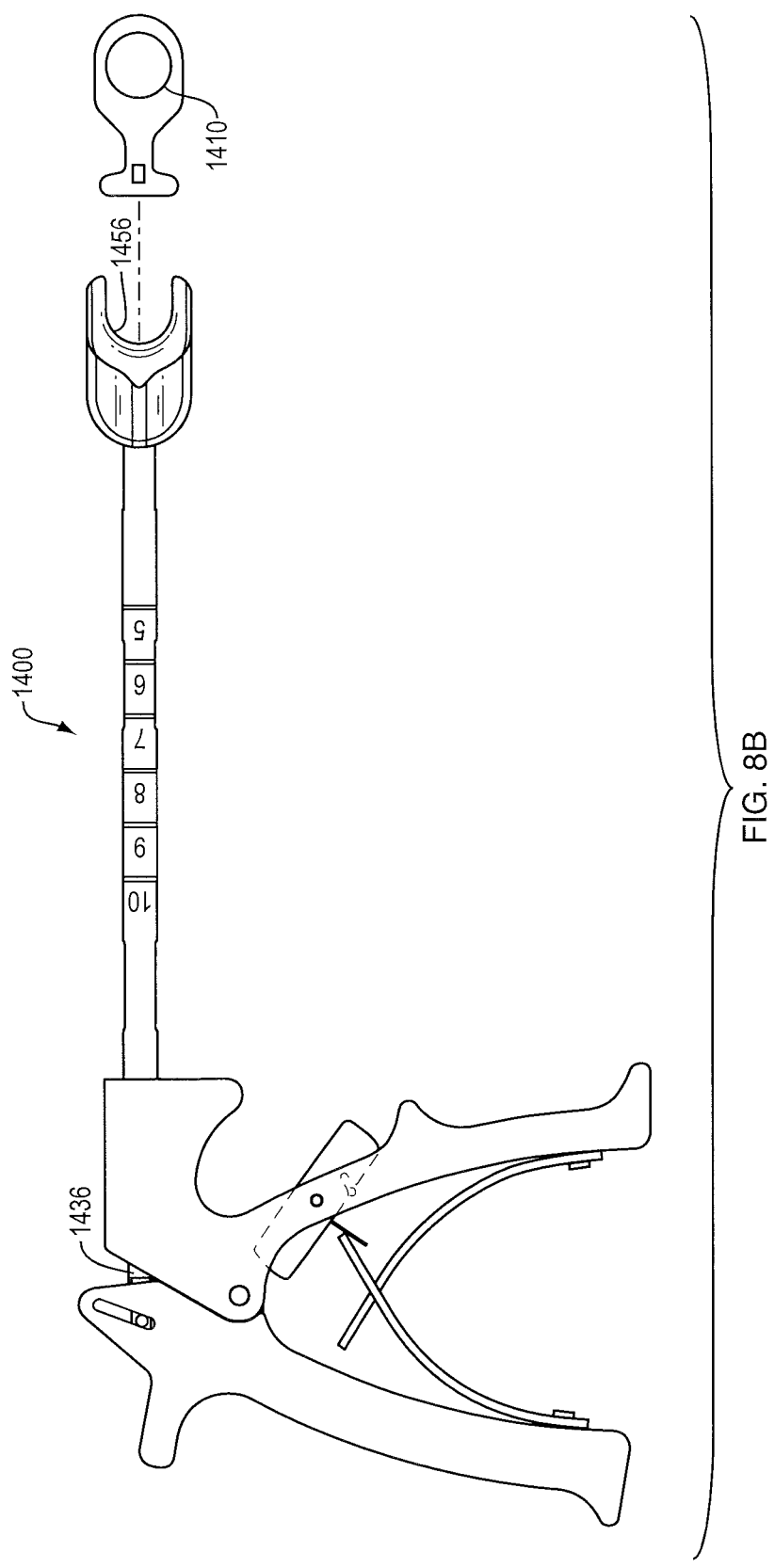
FIG. 8B illustrates a side view of a proximal cutter with the blade shown in exploded form, in accordance with the disclosure.
Figure 8G:
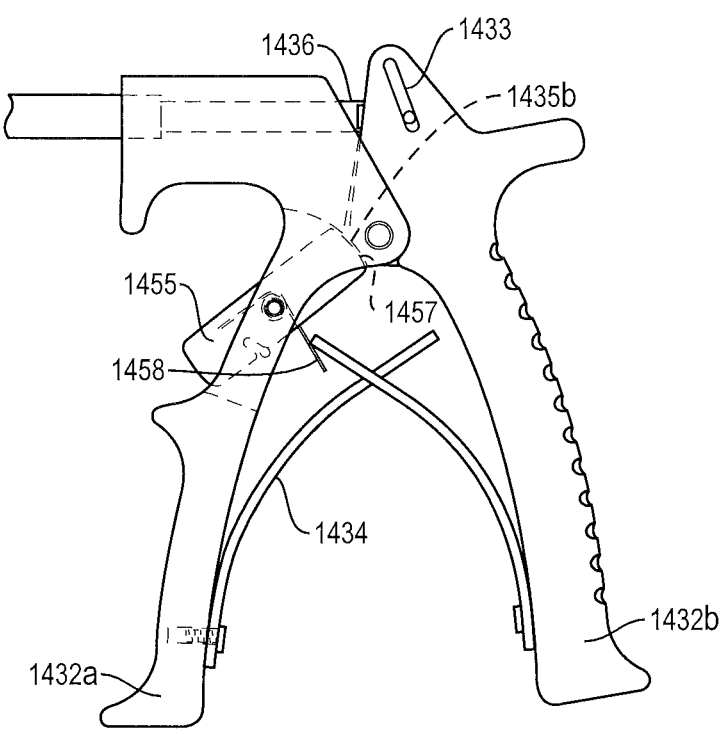
FIG. 8G illustrates a side view of a proximal cutter handle in a locked configuration, in accordance with the disclosure.
Figure 8H:
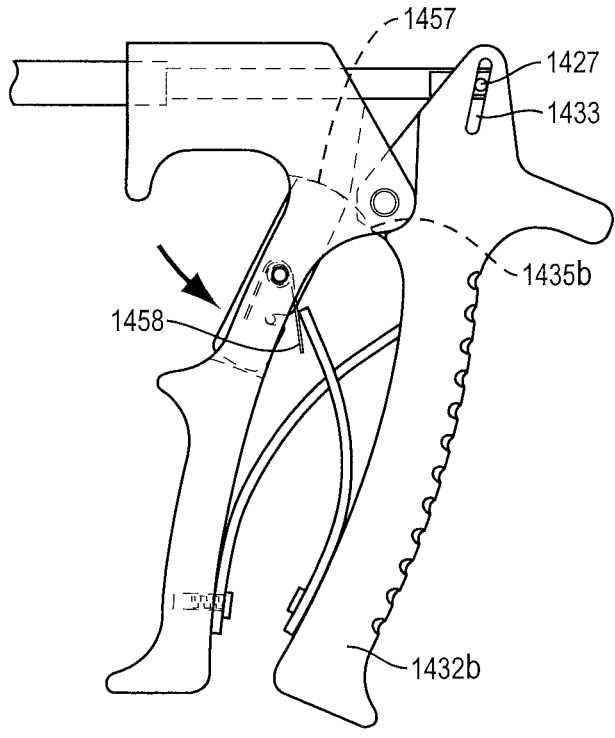
FIG. 8H illustrates a side view of a proximal cutter handle end with the handle unlocked and actuated, in accordance with the disclosure.

Handle 1430 may include a lock out 1455 configured to hinder inadvertent actuation of handle. Lock out 1455 may be operatively coupled to a torsion spring 1458, configured to maintain lock out 1455 in a position that prevents actuation of handle 1432b. An example mechanism is shown in FIG. 8F illustrating a surface 1457 of lock out 1455 that may engage a surface 1435b of handle 1432b, and thereby limit handle rotation. Rotation of locking out 1455 moves surface 1457 away from handle surface 1435b, allowing actuation thereof, shown in FIG. 8G.

Proximal cutter 1400 defines a longitudinal axis L, and levers 1432a, 14232b extend along a first plane through longitudinal axis L. Housing 1452 defines a maximum width Wm for receiving a corresponding maximum width of blade 1410 therein. This orients aperture 1412 such that a central axis through aperture 1412 is perpendicular to the first plane. In use, this orientation preferably orients levers laterally away from graft strip longitudinal axis. Relative to the patient anatomy, this orients the levers 1432a, 1432b either medially or laterally to the patient anatomy. This lever orientation preferably keeps the levers away from the knee joint and out of the field of view along the tendon 50. In addition, guillotine blade 1410 defines a thin planar element have planar surfaces that define the blade thickness, the planar surface extending along a plane that is parallel to shaft longitudinal axis L. Cutting edge 1412a axially translates during actuation, to move towards the handle end 1430. Cutting edge 1412a moves along a plane that is parallel to the first plane and parallel to the shaft longitudinal axis. Cutting edge 1412a defines a segment (arc length) of a 360° (degree) bounded aperture 1412 through the blade thickness, sized to receive an entire cross section of a tendon strip 50' therethrough. 360° (degree) bounded aperture 1412 may also include an arc length 1412b that is configured to dissect tissue, but not as sharp as cutting edge. Arc lengths 1412a, 1412*b* may be opposite each other and may have an extent that is approximately equal in length to each other.

Blade 1410 may operatively couple and detach from pull rod 1436. Connecting portion 1414 may extend along lateral slots of outer shaft 1440 and selectively couple to pull rod 1436. Connecting portion 1414 and pull rod 1436 may include a means to selectively couple and detach from each other. Connecting portion 1414 may include at least one lateral tab 1417 that may aid in detaching the connecting portion 1414 from pull rod 1436. Connecting portion 1414 may include bilateral tabs 1417. Connecting portion 1414 may include aperture 1418 disposed between the tabs 1417 for engaging with a pin or protrusion on pull rod 1436, seen best in cross section image shown in FIG. 8C. Tab(s) 1417 may provide a handle to manipulate the blade 1410, connect, and disconnect it from the pull rod from blade 1410. Tab(s) therefore define a boundary with blunt edges and may be held by the users hand.

In alternative embodiments, housing 1452 and blade 1410 may both be single use, replaceable sub-assembly. In some embodiments, the entire cutter 1400 may be single use. In other embodiments the blade 1410 may be stationary during cutting and housing 1452 may move and advance over the blade 1410.

Figure 9:
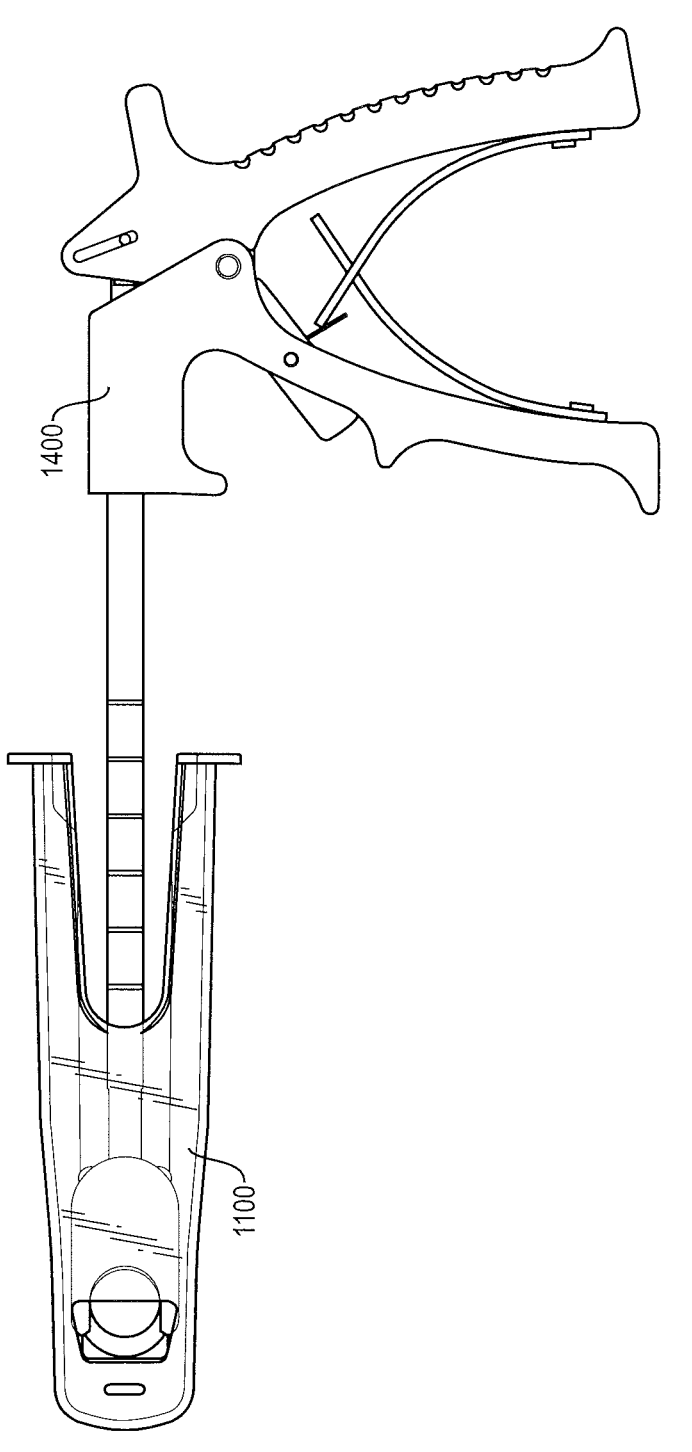
FIG. 9 illustrates a top view of a proximal cutter disposed at a proximal end of the retractor, in accordance with this disclosure.
Figure 10:
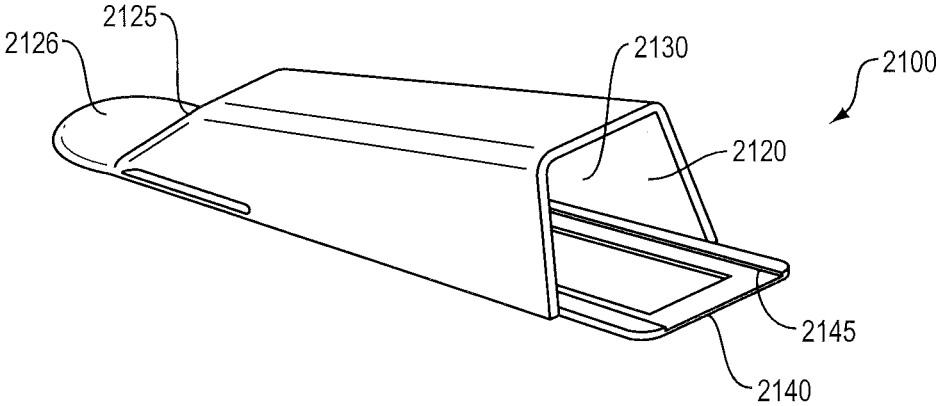
FIG. 10 illustrates an isometric view of another example retractor for accessing a tendon, in accordance with this disclosure.

Proximal cutter 1400 is configured to fit within retractor 1100, with both the guide 1200 and harvester 1300 removed. Housing width Wm may approximate a width W of retractor. Proximal cutter 1400 may slide along graft strip and along retractor 1100 to the proximal end of tendon, seen best in FIG. 9.

FIGS. 10-15 disclose a second system embodiment configured to harvest a tendon. This system includes a retractor 2100 for improving visualization of the tendon, in a manner similar to retractor 1100. The system 2000 may also include at least one modular insert (2150, 2200), a dual harvester 2250 and a proximal cutter 2300. Retractor 2100 includes a means to couple with modular inserts (2150, 2200), that guide the formation of a consistent graft strip from a native QT.

Similar to retractor 1100, retractor 2100 is preferably flexible and may be collapsed and then placed through an incision under the skin. Upon release, retractor 2100 forms a "tent", providing the surgeon visualization of the surgical site. Retractor 2100 may be tapered along its length, having the larger distal opening 2120 for inserting instruments and modular inserts therethrough. Retractor proximal end 2125 may be closed so that tissue and fluid cannot enter the working cavity 2130. Retractor base 2140 may engage an anterior surface of the QT and may include means to engage modular inserts (2150, 2200). Base 2140 may include rails 2145 for example that received inserts (2150, 2200) therein to assist the surgeon in performing the incisions required to harvest the tissue.

More specifically, the system may include a retractor 2100, a longitudinal floor insert 2150, a proximal floor insert 2200, a double blade harvester 2250 for use with the longitudinal floor insert 2200 and a proximal cutter or scalpel 2300 for use with the proximal floor insert 2300.

A method of use may include making an incision through patient's skin near the patella and inserting a proximal end 2125 of retractor 2100 through the incision and advancing it along an anterior surface of the QT. The retractor 2100 may be reduced in profile or collapsed for easier insertion through a skin incision, smaller than the neutral profile of the retractor 2100. Proximal end 2125 may include a lip 2126 that is inserted proximally beyond an end of QT. Retractor base 2140 slides along and lies on the QT anterior surface.

Figure 11:
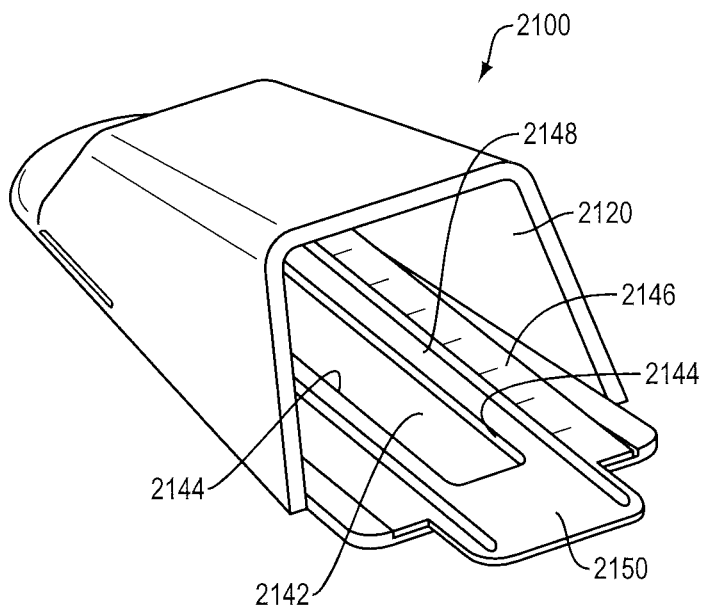
FIG. 11 illustrates an isometric view of the retractor assembled with a first modular insert, in accordance with this disclosure.
Figure 12:
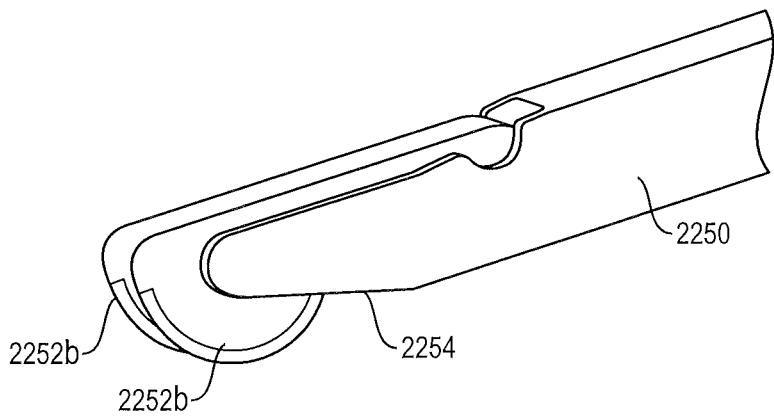
FIG. 12 illustrates a view of another dual blade cutter for harvesting a tendon, in accordance with this disclosure.

Advancing occurs until open end 2120 is adjacent the initial skin incision and may be external to the patient skin, or slightly inserted within and under the skin, while maintaining the incision open. This provide improved visibility of the target tissue and improved access for insertion of instrument and modular inserts. A longitudinal floor 2150 may then be inserted along the base (FIG. 11). This floor 1150 may slide along rails 2145 of base 2140. Floor 1150 may sit on a planar surface of retractor base 2140. Floor 2150 may include an elongate slot 2142 therethrough that may be selected based on the desired graft width and length. Floor 2140 may include markings 2146 to indicate a length. This slot 2142 may define the graft width and length, and may come in a variety of sizes. A cutting tool or harvester, such as harvester 2250 may then be inserted into the retractor's working cavity 2130 and through elongate slot 2142 to dissect a portion of the tendon from the native tendon. Edge surfaces 2144 of elongate slot 2142 may guide trajectory of harvester 2250 Elongate slot may define a 360 degree bounded aperture that may limit translation of harvester 2250 in a proximal and distal direction.

Harvester 2250 may be a double bladed tool, similar to harvester 1300 and may form two parallel cuts into and long the QT simultaneously. The two blades 2252*a* and 2252*b* may be parallel with each other and spaced apart laterally from each other to define a desired width of QT to be cut. At least one of the blades 2252*a* or 2252*b* may slide along one of the edge surfaces 2144 of slot 2142 to keep the cut aligned along the QT. A planar surface 2254 of the harvester 2250 may engage and slide along a top surface 2148 of floor 2150 to control a depth of cut into the QT.

Figure 13:
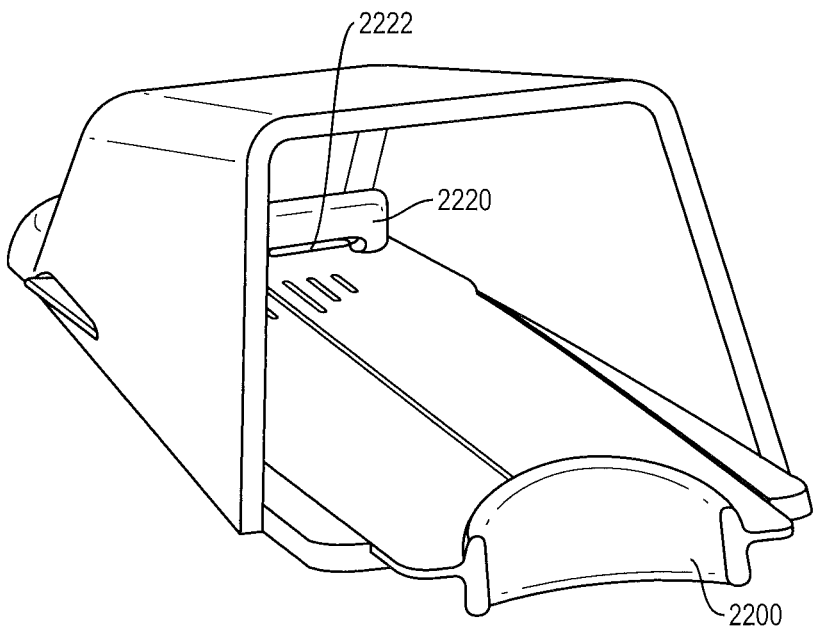
FIG. 13 illustrates an isometric view of the retractor assembled with another modular insert, in accordance with this disclosure.
Figure 14:
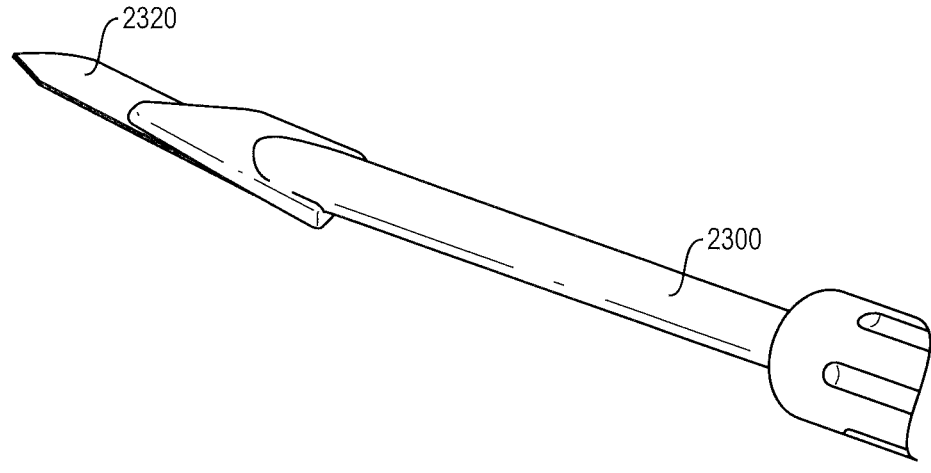
FIG. 14 illustrates a view of a proximal cutter for harvesting a tendon, in accordance with this disclosure.
Figure 15:
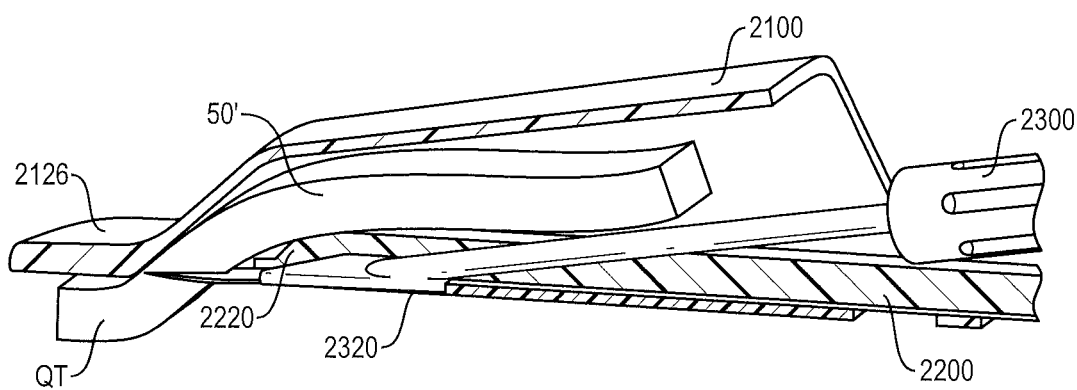
FIG. 15 illustrates a cross section of a cross section transecting a tendon strip, in accordance with this disclosure.

Longitudinal floor 2150 and harvester 2250 may then be removed from base 2140 and through distal opening 2120. Both a posterior side and patella end of the graft may then be cut, by using a scalpel to release the QT graft except for a proximal most end of the remaining graft strip. Proximal floor 2200 may then be installed with base 2140 (FIG. 13). The patella end of graft may be lifted to slide proximal floor 2200 under the graft tissue 50' (see FIG. 15). Proximal floor 2200 includes a graft elevation ramp 2220 at a proximal end that extends at an angle to the floor 2200. Ramp 2220 extends across the width of floor 2200 and includes a slot 2222. A scalpel 2300 may then slide along top surface of floor 2200 and through slot 2222 to amputate the proximal end of graft 50. Scalpel blade 2320 may disposed at a non-zero angle to a shaft and handle, and blade 2320 may be flush on a lower side 2330 to ride along top surface of floor 2200.

Figure 16B:
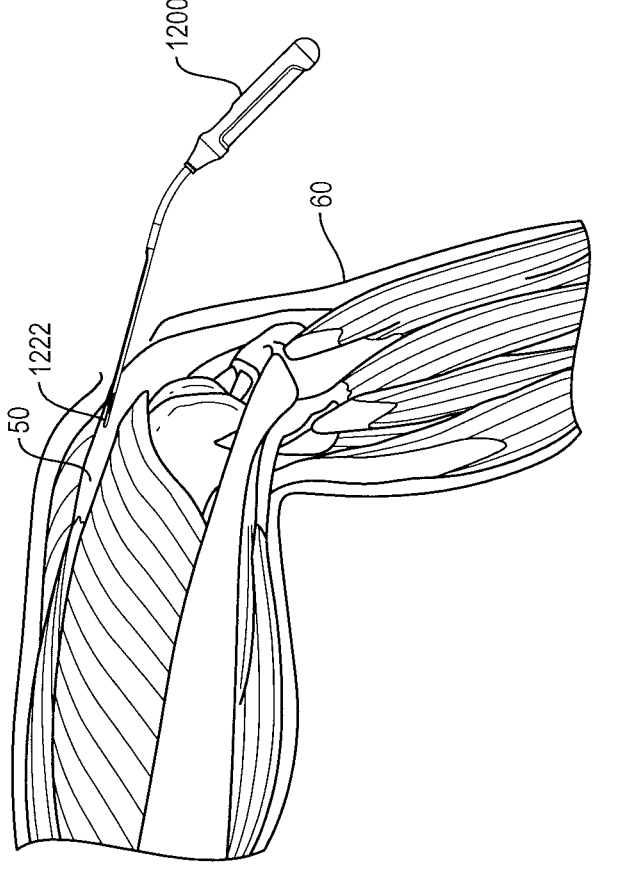
FIGS. 16A-16J illustrate an example method of forming a tendon strip from a native tendon using a system as disclosed.
Figure 16A:
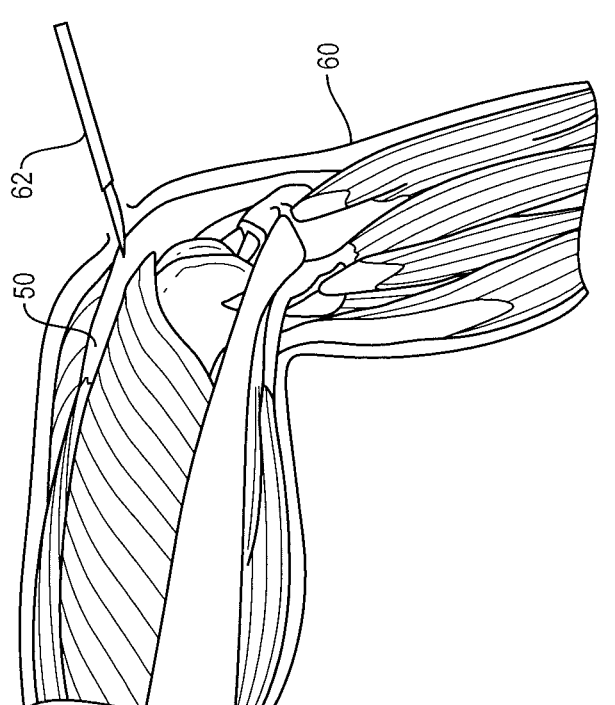
Figure 16D:
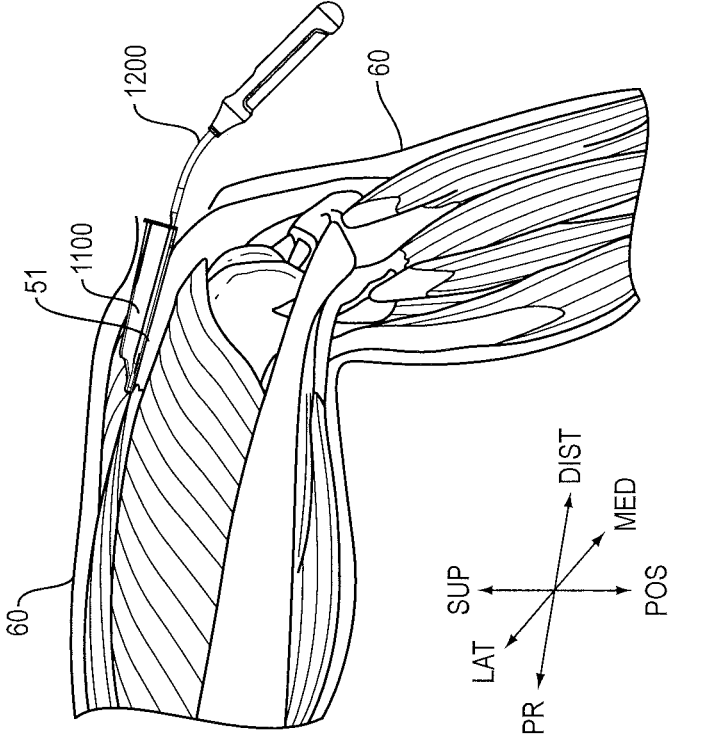
Figure 16C:
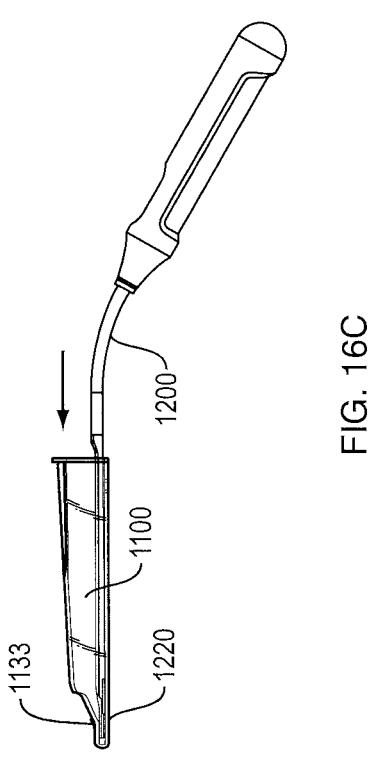

A method of forming a graft is disclosed in FIGS. 16A-16J. The method may begin with making a minimally invasive incision at the superior pole of the patella. (FIG. 16A). This incision 62 may be between 0.5-1 inches in length. Blunt dissector 1200 may then be inserted through incision 62 to dissect around the tendon 50 (FIG. 16B). Blunt dissector 1200 may clear away the fat pad under the skin. Blunt dissector 1200 may perform this separation before inserting the retractor 1100. A dissecting edge 1222 may be configured to separate the tissue layers. Length indicators along a shaft 1230 of blunt dissector 1200 may be used to verify that sufficient length of the tendon 50 has been separated from the subcutaneous layers of the skin. Blunt dissector 1200 may then be removed from under the skin and may be coupled to retractor 1100 (FIG. 16C). Retractor 1100 may include a pocket 1133 configured to receive working end 1220 of blunt dissector 1200 therein. Pocket 1133 may include a plurality of discrete crush ribs 1137 that form a local interference fit between the working end 1220 and pocket 1133, to improve the grip. Once correctly engaged with each other, the user may receive positive feedback, such as an audible click. Pocket 1133 may include an opening 1134 that receives a tab 1226 upon correct insertion, the insertion of this tab 1226 into the opening 1134 providing the audible feedback. Retractor 1100 is preferably formed of a flexible material and pocket 1133 may both elastically and plastically deform while operatively coupling to blunt dissector working end 1220. For example, the crush ribs 1137 may plastically deform, while the pocket 1133 may elastically deform. Coupling the blunt dissector 1200 to the retractor 1100 orients a guiding surface of the blunt dissector 1200 along a length of the retractor 1100. The guiding surface is configured to guide a trajectory and translation extent of harvesting tools and thereby form a consistent graft tendon strip. Optionally a guide tool, different than blunt dissector 1200 may be coupled to the retractor 1100 to orient a guiding surface along the retractor. For example, a modular insert similar to floor 2150 may be operatively coupled to a base of a retractor 1100.

With shaft and handle end of blunt dissector 1200 extending from retractor end 1120, retractor 1100 may be inserted through skin incision 62 and along tendon 50 (FIG. 16D). Retractor 1100 is preferably flexible, and as such, inserting the retractor 1100 may include collapsing or deforming the retractor, using external forces, to fit through the skin incision. These external forces may come from a device, a surgeon's hand and/or the patient's anatomy. For example, wings 1112a, 1112b may be flexed medially during insertion (illustrated in FIG. 3). Flexing the wings 1112a, 1112b allows the retractor 1100 to b e reduced in profile and pass through a relatively smaller incision. Retractor wings 1112a, 1112b may be released once mostly under the skin 60 and within the subcutaneous layer between the tendon anterior surface 51 and below the skin. Blunt dissector 1200 may be used to position the retractor 1100 along the tendon in the target orientation with the retractor end 1120 adjacent or coincident with skin incision 62. Release of external forces on the retractor 1100 tents the skin away from the tendon anterior surface 51. This presents the surgeon with a retracted opening at the skin incision, corresponding with distal opening 1120 with a tented working cavity and access to the tendon. Preferably, the retractor 1100 remains stationary and defines a working cavity at least as long as the target tendon strip length, and wider than the target graft strip width. Preferably, the working cavity is wider than the entire width of the target tendon. Insertion may be complete when a distal radial flange (1117a, 1117b) abuts the incision 62. Flanges 1117a, 1117b may engage outer skin surface, limiting further retractor translation under the skin.

Optionally the retractor 1100 may be inserted at least partially through the incision without the blunt dissector 1200 assembled, and the blunt dissector 1200 may be inserted after the retractor 1100 is mostly in place. The retractor 1100 may be more fully collapsed or reduced in profile when free of the blunt dissector 1200, which may allow the skin incision to remain smaller. Collapsing of the retractor to a minimal profile is facilitated by the combination of the plurality of openings and reliefs through the retractor 1100 together with the retractor flexibility. Following along with this example method, the retractor 1100 may be at least partially inserted through the skin incision in the collapsed configuration and once mostly under the skin, may be released to tent the skin away from the QT anterior surface. The blunt dissector 1200 may then be inserted through the skin incision 62, along the retractor 1100 and into the pocket 1133. The user may be manipulate the dissector 1200 within the pocket 1133 until a feedback is detected indicating that tab 1226 has been engaged with opening 1134, and therefore the blunt dissector 1200 is correctly inserted within pocket 1133.

Figure 16F:
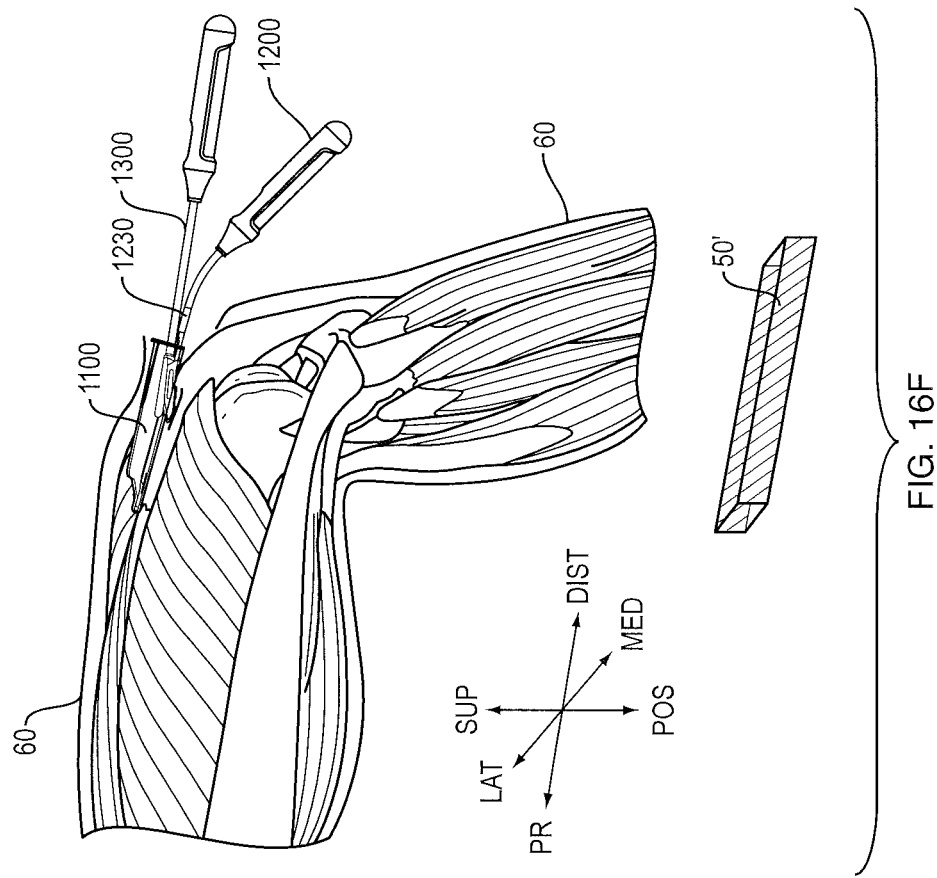
Figure 16E:
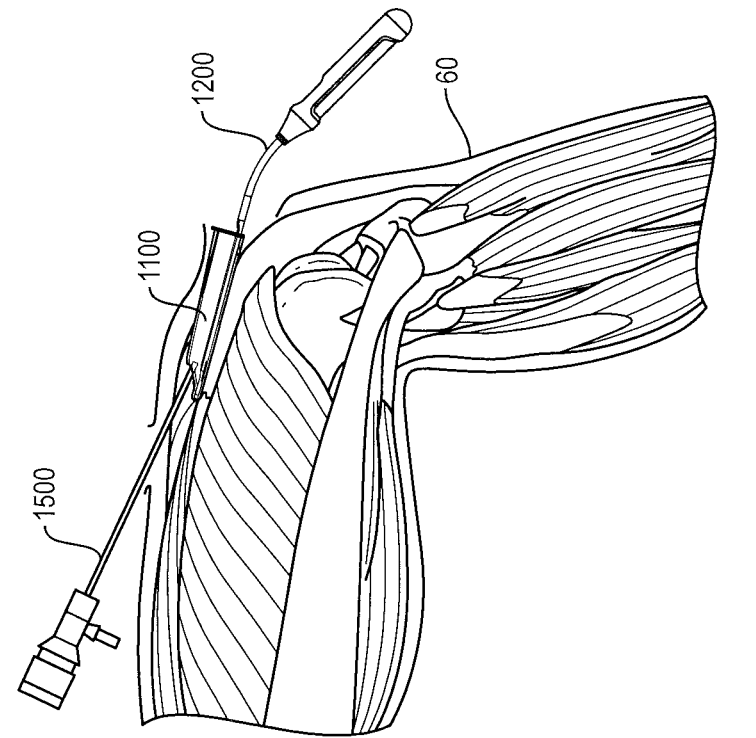

Optionally, shown in FIG. 16E, a second port through the skin 60 at a proximal end of tendon 50 may be formed and a scope 1500 and/or light source may be placed through an aperture 1115 of retractor 1100. A target width and depth of tendon strip may then be determined, and a working end of a harvester 1300 may then be selected and assembled, corresponding to these targeted values. For example, a harvester 1300 may be chosen, configured to form two lateral cut sides of the tendon strip 50', defining a tendon strip width of about 8 mm. Other widths may include a 10 mm wide strip, or a 12 mm wide strip. Harvester 1300 may then be inserted through retractor end 1120 and into working cavity (FIG. 16F). Harvester 1300 engages shaft 1230 of dissector 1200 to guide trajectory of blades 1340 into and along the tendon 50. This forms both lateral sides of the graft strip simultaneously. Harvester 1300 may include a channeled surface 1324 disposed between the two blades 1340 that slides along a superior surface of the dissector shaft 1230 to limit the depth of cut into the tendon and also the trajectory of the two lateral cuts along the tendon 50 to the proximal end of the tendon. In other embodiments, the harvester 1200 may include a single blade, and only one lateral side may be formed at this stage. The dissector shaft 1230 may engage an anterior surface of the tendon 50 while the harvester 1300 is translated. The retractor end 1120 allows access to both the dissector 1100 and harvester 1300 simultaneously, while providing visibility therethrough of the target tendon. The blunt dissector 1200 may include at least one edge 1225 that limits the extent of the harvester proximal trajectory. The harvester 1300 therefore may slide along the dissector shaft up until it abuts this edge 1225. The harvester 1300 may define arced blade edges such that retraction along the dissector shaft, towards the knee may also form lateral sides of the graft strip, or at least separate some remaining tissue bridges between the graft strip lateral sides and remaining tendon 50. The harvester channel 1324 may be contoured such that a depth of cut into the tendon 50 is relatively consistent along the length of the cuts, despite the angle of approach of the harvester 1300. The harvester 1300 may begin cutting at a distal end at a first angle of approach, with a distal curved contoured portion of the channel 1324 engaging the shaft 1230. The angle of approach may gradually become shallower as the harvester is advanced proximally such that a linear surface 1324b of the channel 1324 may engage the shaft to limit a depth of cutting into to QT.

Figure 16H:
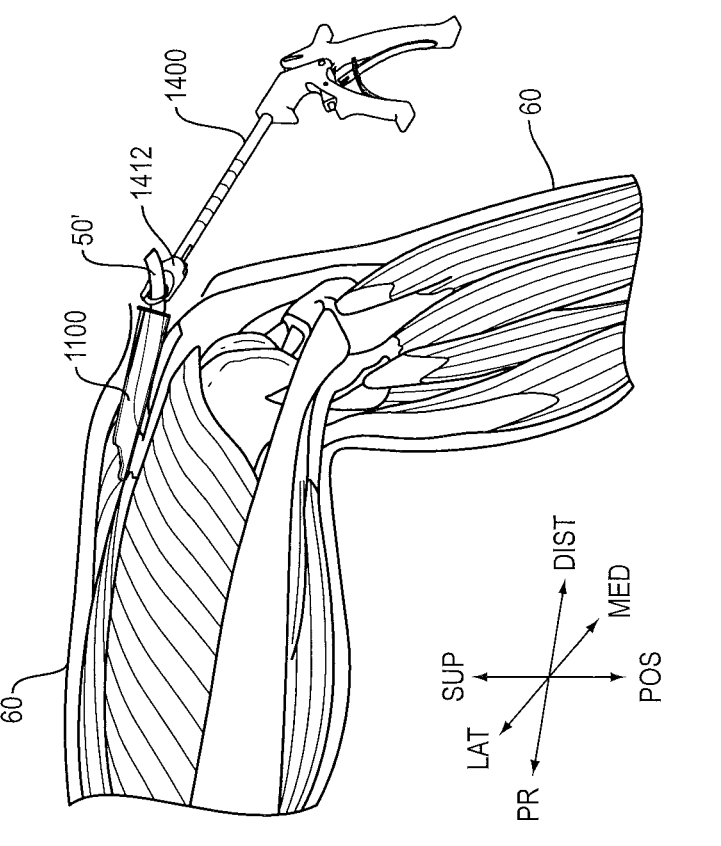
Figure 16G:
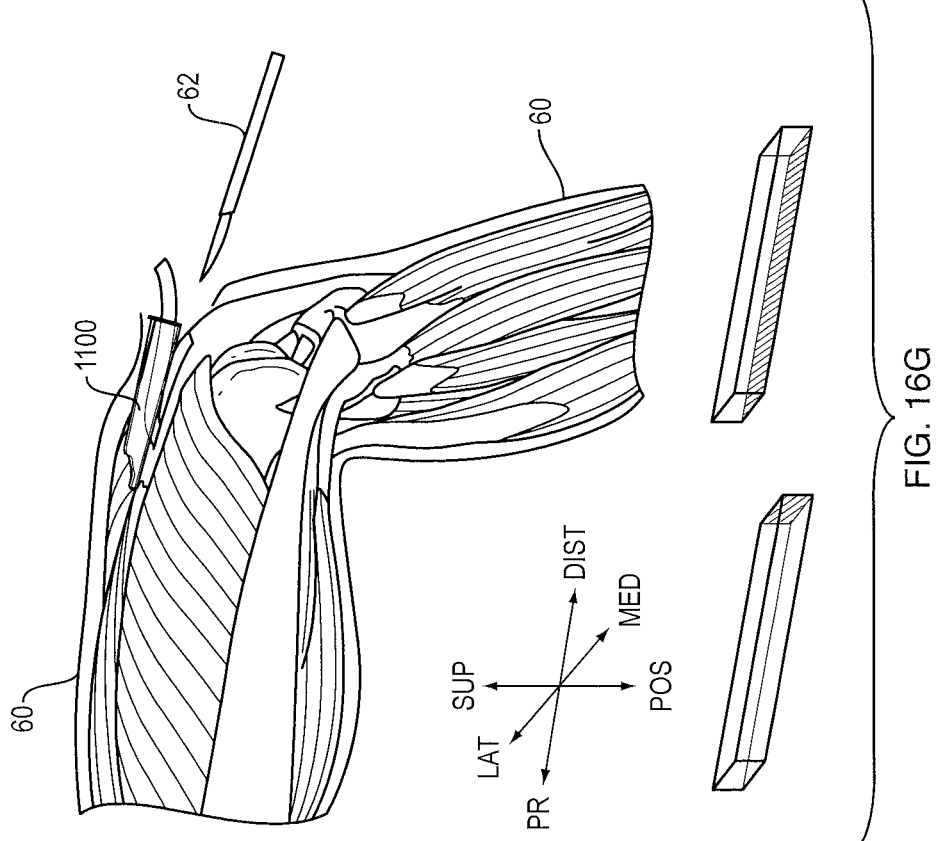
Figures 16I, 16J:
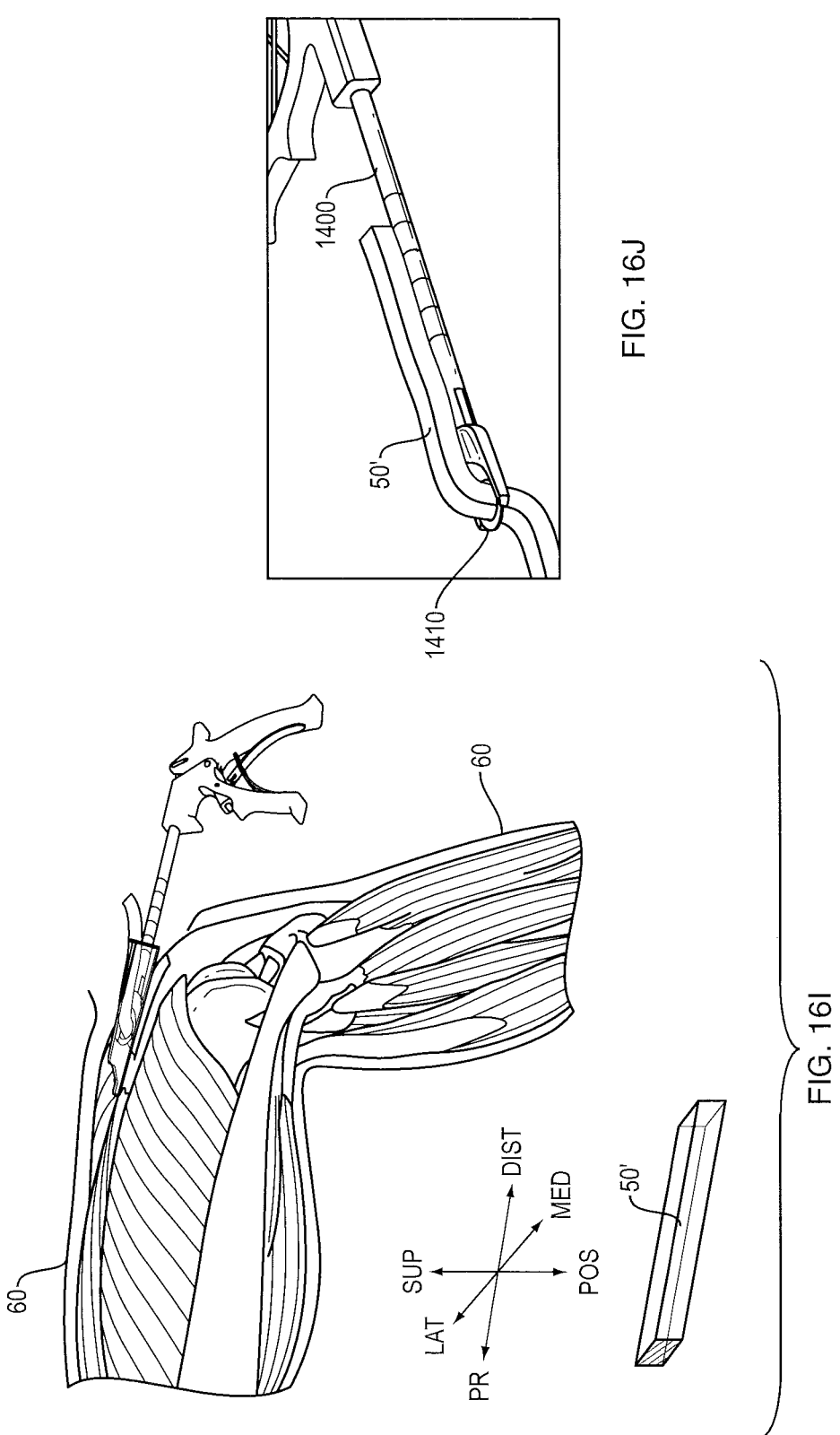

The dissector 1200 and harvester 1300 may then be removed, leaving the retractor 1100 in situ. As shown in the graphic in FIG. 16F the two lateral side surfaces of the strip 50' are now separated from the native tendon 50. The distal and posterior separation may then be performed, represented in FIG. 16G, such that the graft strip 50' is only coupled at a proximal most end to the native tendon 50. This separation may be performed with a scalpel, with the retractor 1100 remaining in place. Distal end of graft strip may then be threaded through an aperture 1412 of proximal cutter 1400 (FIG. 16H). Graft strip may be fed through aperture 1412 and working end of proximal cutter 1400 may extend through retractor end 1120 along strip to the proximal end of graft strip, illustrated in FIG. 16I. FIG. 16J illustrates a close up of proximal cutter 1400 with the strip 50' extending through aperture and the retractor 1100 removed for simplicity of understanding. Levers of proximal cutter 1400 may extend either medially or laterally away from knee for improved visibility. Lock out member 1455 of proximal cutter 1400 may then be moved and the proximal cutter 1400 actuated to amputate the graft strip 50'. Blade 1410 is retracted into housing 1452 to amputate the graft strip 50' Graft strip 50', proximal cutter 1400 and retractor 1100 may then be removed.

One skilled in the art will realize the disclosure may be embodied in other specific forms without departing from the spirit or essential characteristics thereof. The foregoing examples are therefore to be considered in all respects illustrative rather than limiting of the disclosure described herein. Scope of the disclosure is thus indicated by the appended claims, rather than by the foregoing description, and all changes that come within the meaning and range of equivalency of the claims are therefore intended to be embraced therein.

We claim:

1. A retractor that is self-supporting for holding open an anatomic space developed in a patient for harvesting a tendon therein, said retractor comprising;

an elongate body defining a proximal end, a distal end, a roof that defines a curved surface and a floor that defines a planar surface for engaging an anterior surface of the tendon, the elongate body defining an elongate working cavity extending from the distal end;

wherein the roof includes at least one opening defining bilateral wings at a distal end of the elongate body, and wherein the elongate body is configured to be elastically collapsed from a neutral configuration to a collapsed configuration by external forces on the bilateral wings, for insertion through a skin incision, and upon release of the external forces the elongate body is configured to relax towards the neutral configuration and hold the anatomic space open without external support; and a means of engaging a cutting guide located at the distal end, the means of engaging orienting the cutting guide along the working cavity.

2. The retractor of claim 1 wherein the roof includes a roof relief at a proximal end of the elongate body, the roof relief defining a 360 degree bounded aperture configured to decrease a profile of the retractor in the collapsed configuration.

3. The retractor of claim 1 wherein floor includes an elongate opening therethrough, the elongate opening having a width greater than an entire tendon width.

4. The retractor of claim 1 wherein the means of engaging and orienting, orients a shaft of the cutting guide along the working cavity and parallel to a longitudinal axis of the elongate body.

5. The retractor of claim 1 wherein the means of engaging and orientating includes a pocket extending from a proximal end of the working cavity, for receiving a cutting guide end therein.

6. The retractor of claim 5 wherein the retractor is configured to provide audible feedback upon correct engagement of the cutting guide within the pocket.

7. The retractor of claim 1 wherein the distal end defines an entrance into the working cavity, for receiving a guide tool and a harvesting tool simultaneously therethrough.

8. A retractor that is self-supporting for holding open an anatomic space developed in a patient for harvesting a tendon, said retractor comprising;

an elongate body formed of a flexible material including a proximal end, a distal end, a longitudinal axis, a roof having a curved surface and a floor having a planar surface for engaging an anterior surface of the tendon, the elongate body defining a working cavity extending from the distal end;

wherein the distal end defines bilateral wings having free distal most ends, the roof having an elongate opening that defines a roof boundary of the bilaterial wings, wherein the bilateral wings are configured to be pinched towards each other to temporarily reduce a profile of the retractor for insertion through a skin incision, and upon release the bilateral wings are configured to relax away from each other such that the retractor tents the anatomic space open without external support.

9. The retractor of claim 8 wherein the retractor includes a roof relief at a proximal end, the roof relief defining a 360 degree bounded hole configured to increase flexibility of the retractor and reduce a profile of the retractor during insertion through the skin incision.

10. The retractor of claim 8 wherein the floor includes an elongate opening therethrough defining a floor boundary of the bilateral wings.

11. The retractor of claim 8 further comprising a pocket extending from a proximal end of the working cavity, for receiving a cutting guide end therein.

12. The retractor of claim 11 wherein the pocket includes a tab opening, configured to engage with a cutting guide tab, the tab opening configured to provide audible feedback upon engagement between the tab opening and tab.

13. The retractor of claim 8 wherein the distal end defines an entrance into the working cavity, for receiving a guide tool and a harvesting tool simultaneously therein.

14. A system for harvesting a tendon graft from a tendon comprising:

a retractor that is self-supporting for holding open an anatomic space developed in a patient above the tendon, the retractor comprising a flexible elongate body including a proximal end, a distal end, a longitudinal axis, a roof having a curved surface and a floor having a planar surface for engaging an anterior surface of the tendon, the flexible elongate body defining an elongate working cavity extending from the distal end;

a guide defining a handle end, a working end and an elongate shaft extending therebetween; wherein the guide is configured to assemble with the retractor and orient the elongate shaft along the elongate working cavity;

a harvesting tool defining a handle end and a working end with an elongate shaft extending therebetween, the harvesting tool working end including a blade edge for cutting into the tendon and a contoured surface for engaging the elongate shaft of the guide while translating along the elongate shaft of the guide while in the working cavity, the elongate shaft of the guide and contoured surface configured to cooperate to limit a depth of cut, trajectory and translation extent of the blade edge relative to the tendon.

15. The system of claim 14 wherein the retractor defines bilateral wings having free distal most ends, wherein the bilateral wings are configured to be pinched towards each other to temporarily reduce a profile of the retractor for insertion through a skin incision, and upon release the bilateral wings are configured to relax away from each other and tent the anatomic space open without external support.

16. The system of claim 14 wherein the retractor includes a pocket extending from a proximal end of the working cavity, for receiving the working end of the guide therein and thereby orienting the guide shaft along the working cavity.

17. The system of claim 14 wherein the retractor defines a distal opening sized to receive both the guide and the harvesting tool simultaneously therethrough.

18. The system of claim 14 further comprising a proximal cutter, configured to extend along the working cavity and transect a tendon graft.

* * * * *